(12) United States Patent
Getts et al.

(10) Patent No.: US 10,471,093 B2
(45) Date of Patent: *Nov. 12, 2019

(54) MODIFIED IMMUNE-MODULATING PARTICLES

(71) Applicant: Cour Pharmaceuticals Development Company, Elmhurst, IL (US)

(72) Inventors: Daniel R. Getts, Washington, DC (US); Rachael Terry, Petersham (AU); Nicholas King, Petersham (AU)

(73) Assignee: Cour Pharmaceuticals Development Company., Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,461

(22) Filed: Feb. 17, 2015

(65) Prior Publication Data

US 2015/0174155 A1 Jun. 25, 2015

Related U.S. Application Data

(63) Continuation of application No. 13/884,817, filed as application No. PCT/US2011/060537 on Nov. 14, 2011, now abandoned.

(60) Provisional application No. 61/413,018, filed on Nov. 12, 2010, provisional application No. 61/413,016, filed on Nov. 12, 2010.

(51) Int. Cl.
| | |
|---|---|
| *A61K 9/00* | (2006.01) |
| *A61K 31/765* | (2006.01) |
| *A61K 9/10* | (2006.01) |
| *A61K 31/19* | (2006.01) |

(52) U.S. Cl.
CPC .......... *A61K 31/765* (2013.01); *A61K 9/0019* (2013.01); *A61K 9/10* (2013.01); *A61K 31/19* (2013.01); *Y02A 50/393* (2018.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,804,201 A | 9/1998 | King | |
| 5,871,747 A | 2/1999 | Gengoux-Sedlik et al. | |
| 6,004,763 A | 12/1999 | Gengoux et al. | |
| 7,829,113 B2 | 11/2010 | Okada et al. | |
| 2002/0131960 A1 | 9/2002 | Sadelain | |
| 2003/0166509 A1 | 4/2003 | Edwards | |
| 2004/0043075 A1* | 3/2004 | Ritter et al. | 424/490 |
| 2004/0072749 A1 | 4/2004 | Zochoer et al. | |
| 2005/0002999 A1 | 1/2005 | Mehta et al. | |
| 2006/0088542 A1 | 4/2006 | Braun | |
| 2007/0014752 A1 | 1/2007 | Roy et al. | |
| 2007/0041934 A1 | 2/2007 | William et al. | |
| 2007/0190160 A1 | 8/2007 | Turos et al. | |
| 2008/0039816 A1 | 2/2008 | Svarovsky et al. | |
| 2008/0124350 A1 | 5/2008 | Mumper et al. | |
| 2008/0207515 A1 | 8/2008 | Ferguson et al. | |
| 2008/0268552 A1 | 10/2008 | Geiger et al. | |
| 2008/0311140 A1 | 12/2008 | Lee et al. | |
| 2009/0123509 A1 | 5/2009 | Berkland et al. | |
| 2009/0214474 A1 | 8/2009 | Jennings | |
| 2009/0304726 A1 | 12/2009 | Solomon et al. | |
| 2009/0325931 A1 | 12/2009 | Rossi et al. | |
| 2010/0008920 A1 | 1/2010 | Schneck et al. | |
| 2010/0015060 A1 | 1/2010 | Baldi | |
| 2010/0028450 A1 | 2/2010 | Vasu | |
| 2010/0055189 A1 | 3/2010 | Hubbell et al. | |
| 2010/0151000 A1 | 6/2010 | Thomas et al. | |
| 2010/0303850 A1 | 12/2010 | Lipford et al. | |
| 2011/0014292 A1 | 1/2011 | O'Hehir | |
| 2011/0135666 A1 | 6/2011 | Tedder et al. | |
| 2011/0135744 A1 | 6/2011 | Chin | |
| 2011/0150987 A1 | 6/2011 | Saint-Lu et al. | |
| 2011/0182805 A1 | 7/2011 | Desimone | |
| 2011/0206773 A1 | 8/2011 | Lavik et al. | |
| 2011/0212172 A1 | 9/2011 | Kellum | |
| 2012/0076831 A1 | 3/2012 | Miller et al. | |
| 2012/0263653 A1 | 10/2012 | Podobinski | |
| 2012/0276109 A1 | 11/2012 | Fraser et al. | |
| 2012/0276134 A1 | 11/2012 | Fraser et al. | |
| 2012/0276155 A1 | 11/2012 | Kishimoto et al. | |
| 2012/0276156 A1 | 11/2012 | Fraser et al. | |
| 2012/0276157 A1 | 11/2012 | Fraser et al. | |
| 2012/0276158 A1 | 11/2012 | Fraser et al. | |

(Continued)

FOREIGN PATENT DOCUMENTS

| | | |
|---|---|---|
| CA | 2740960 A1 | 4/2009 |
| EP | 2057998 A1 | 5/2009 |

(Continued)

OTHER PUBLICATIONS

Muthu MS. Asian J. Pharm. 2009; 3: 266-273.*
Salvador-Morales C, et al. Biomaterials. 2009; 30(12): 2231-2240.*
Sampson BA et al. Ann NY Acad. Sci. 2001; 951: 172-178.*
Frohlich, et al., "The Role of Surface Charge in Cellular Uptake and Cytotoxicity of Medical Nanoparticles," International Journal of Nanomedicine, 7(31):5577, Oct. 2012.
International Search Report for PCT/US2011/060537 dated Feb. 20, 2013, 3 pages.
International Search Report for PCT/US2014/026719 dated Sep. 26, 2014, 7 pages.
McCauley, et al., "Comprehensive Follow-Up of the First Genome-Wide Association Study of Multiple Sclerosis Identifies KIF21B and TMEM39A as Susceptibility Loci, The International Multipke Sclerosis Genetics Consortium (IMSGC)," Human Molecular Genetics, 19(5):953-962, 2010.

(Continued)

*Primary Examiner* — David Browe
(74) *Attorney, Agent, or Firm* — Marshall, Gerstein & Borun LLP

(57) ABSTRACT

The current invention involves the surprising finding that when carboxylated particles, such as carboxylated polystyrene, PLGA, or diamond particles are administered to subjects, inflammatory immune responses are ameliorated. Additionally, the present invention describes methods of treating inflammatory diseases by administering these same carboxylated particles.

9 Claims, 17 Drawing Sheets

Specification includes a Sequence Listing.

(56) References Cited

U.S. PATENT DOCUMENTS

| | | |
|---|---|---|
| 2012/0276159 A1 | 11/2012 | Fraser et al. |
| 2012/0276160 A1 | 11/2012 | Maldonado |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0011824 A1 | 1/2013 | Chan |
| 2013/0028941 A1 | 1/2013 | Altreuter et al. |
| 2013/0039954 A1 | 2/2013 | Pittet et al. |
| 2013/0059009 A1 | 3/2013 | Kishimoto et al. |
| 2013/0202659 A1 | 8/2013 | Crawford et al. |
| 2013/0323319 A1 | 12/2013 | Getts et al. |
| 2014/0030344 A1 | 1/2014 | Zepp et al. |
| 2014/0193453 A1 | 7/2014 | Zepp et al. |
| 2014/0199340 A1 | 7/2014 | Maldonado |
| 2014/0242173 A1 | 8/2014 | Zepp et al. |
| 2015/0010631 A1 | 1/2015 | Getts |
| 2015/0174155 A1 | 6/2015 | Getts et al. |
| 2015/0190485 A1 | 7/2015 | Shea et al. |
| 2015/0209293 A1 | 7/2015 | Shea et al. |
| 2015/0283218 A1 | 10/2015 | Shea et al. |
| 2016/0166664 A1 | 6/2016 | Miller et al. |

FOREIGN PATENT DOCUMENTS

| | | |
|---|---|---|
| EP | 2123261 A1 | 11/2009 |
| EP | 2255831 A1 | 12/2010 |
| JP | H06157592 A | 6/1994 |
| WO | WO 01/12222 A1 | 2/2001 |
| WO | WO 03/043586 A2 | 5/2003 |
| WO | WO 03/092654 A1 | 11/2003 |
| WO | WO-2007/087341 A2 | 8/2007 |
| WO | WO-2008/109852 A2 | 9/2008 |
| WO | WO-2009/051837 A2 | 4/2009 |
| WO | WO-2009/052561 A1 | 4/2009 |
| WO | WO-2009/056332 A1 | 5/2009 |
| WO | WO-2010/025324 A2 | 3/2010 |
| WO | WO-2010/025324 A3 | 6/2010 |
| WO | WO-2010/066049 A1 | 6/2010 |
| WO | WO 2010/085509 | 7/2010 |
| WO | WO-2011/031441 A1 | 3/2011 |
| WO | WO-2011/103588 A1 | 8/2011 |
| WO | WO-2011/133617 A1 | 10/2011 |
| WO | WO-2011/150573 A1 | 12/2011 |
| WO | WO 2011/153532 | 12/2011 |
| WO | WO-2012/001647 A2 | 1/2012 |
| WO | WO-2012/018380 A2 | 2/2012 |
| WO | WO-2012/019041 A2 | 2/2012 |
| WO | WO 2012/065153 | 5/2012 |
| WO | WO-2012/071014 A1 | 5/2012 |
| WO | WO-2012/101638 A2 | 8/2012 |
| WO | WO 2012/149252 | 11/2012 |
| WO | WO 2012/149255 | 11/2012 |
| WO | WO 2012/149454 | 11/2012 |
| WO | WO-2013/192532 A2 | 12/2013 |
| WO | WO-2014/160465 A2 | 10/2014 |
| WO | WO-2015/023796 A2 | 2/2015 |

OTHER PUBLICATIONS

Schrand, et al., "Nanodiamond Oarticles: Properties and Perspectives for Bioapplications," Critical Reviews in Solid State and Materials Sciences, 34:18-74, 2009.

Lo et al., "Simultaneous release of multiple molecules from poly(lactide-co-glycolide) nanoparticles assembled onto medical devices", Biomaterials, 30: 4889-4897 (2009).

Lunov et al., "The effect of carboxydextran-coated superparamagnetic iron oxide nanoparticles on c-Jun N-terminal kinase-mediated apoptosis in human macrophages," Biomaterials 31:5063-5071 (2010).

Schmidt et al., "Glucocorticoids Induce Apoptosis in Human Monocytes: Potential Role of IL-1β," J. Immunol. 163:3484-3490 (1999).

Tse, "Particulate promotion of tolerance", Nature Rev Drug Discovery, 12: 22-23 (2013).

"Accidental Injection of Topical Thrombin Continues", Institute for Safe Medication Practices, downloaded from the Internet at: <https://www.ismp.org/resources/accidental-injection-topical-thrombin-continues> (Jan. 12, 2017).

Belikoff et al., A Practical Approach to Animal Models of Sepsis, In: Conn et al. (eds), Sourcebook of Models for Biomedical Research. Humana Press (2008).

Cuzzocrea et al., Protective effect of melatonin in a non-septic shock model induced by zymosan in the rat, J. Pineal Res., 25(1):24-33 (Aug. 1998).

Sadrieh, Overview of CDER Experience with Nanotechnology-related Drugs, Advisory Committee for Pharmaceutical Science and Clinical Pharmacology, U.S. Food and Drug Administration (Aug. 9, 2012).

Taylor, Ocular immune privilege, Eye (Lond.), 23(10):1885-9 (Oct. 2009).

Batanero et al., "Biodegradable poly (DL-lactide glycolide) microparticles as a vehicle for allergen-specific vaccines: a study performed with Ole e 1, the main allergen of olive pollen," J. Immunol. Meth. 259:87-94 (2002).

Battaglia, et al. Rapamycin and Interleukin-10 Treatment Induces T Regulatory Type 1 Cells That Mediate Antigen-Specific Transplantation Tolerance, Diabetes. Jan. 2006, vol. 55, pp. 40-49.

Chauhan, et al. "Unexpected In Vivo Anti-Inflammatory Activity Observed for Simple, Surface Functionalized Poly(amidoamine) Dendrimers." Biomacromolecules. Apr. 6, 2009, vol. 10, pp. 1195-1202.

Cour Pharmaceuticals Development Company et al., "Immune-Modifying Particles for the Treatment of Ebola Virus," PCT Appl. No. PCT/US2015/054922, 52 pages (filed Oct. 9, 2015).

Dobrovolskaia et al., "Immunological properties of engineered nanomaterials," Nat. Nanotechnol. 2:469-478 (2007).

Dolgin. The inverse of immunity. Nature Medicine. 2010; 16(7):740-743.

Eagar, et al. CTLA-4 regulates expansion and differentiation of Th1 cells following induction of peripheral T cell tolerance. J Immunol. Jun. 15, 2004;172(12):7442-50.

Eagar, et al. The role of CTLA-4 in induction and maintenance of peripheral T cell tolerance. Eur J Immunol. Apr. 2002;32(4):972-81.

Eldridge, et al., "Biodegradable and biocompatible poly(DL-lactide-co-glycolide) microspheres as an adjuvant for staphylococcal enterotoxin B toxoid which enhances the level of toxin-neutralizing antibodies," Infection and Immunity, 59(9):2978-2986, 1991.

Getts et al., "Microparticles bearing encephalitogenic peptides induce T-cell tolerance and ameliorate experimental autoimmune encephalomyelitis", Nature Biotechnol, 30:1217-1224 (2012).

Getts, et al. Current landscape for T-cell targeting in autoimmunity and transplantation. Immunotherapy. Jul. 2011;3(7):853-70.

Getts, et al. Tolerance induced by apoptotic antigen-coupled leukocytes is induced by PD-LI1+ and IL-10-producing splenic macrophages and maintained by T regulatory cells. J Immunol. Sep. 1, 2011; 187(5):2405-17. Epub Aug. 5, 2011.

Hsu, et al. IL-33 Is Produced by Mast Cells and Regulates IgE Dependent Inflammation. PLoS One. Aug. 3, 2010;5(8):e11944.

Hunter et al., "A Biodegradable Nanoparticle Platform for the Induction of Antigen-Specific Immune Tolerance for Treatment of Autoimmune Disease," ACS Nano 8(3):21482160 (2014).

Jilek, et al. "Modulation of allergic responses in mice by using biodegradable poly(lactide-co-glycolide) microspheres" J Allergy Clin Immunol 2004, vol. 114: 943-950 Available online Aug. 3, 2004.

Kanno, et al. A murine scavenger receptor MARCO recognizes polystyrene nanoparticles. Toxicol Sci. Jun. 2007;97(2):398-406. Epub Mar. 14, 2007.

Keijzer, et al. "PLGA, PLGA-TMC and TMC-TPP Nanoparticles Differentially Modulate the Outcome of Nasal Vaccination by Inducing Tolerance or Enhancing Humoral Immunity," PLOS One Nov. 2, 2011, vol. 6(11) e26684, 10 pages.

Kennedy et al., "Induction of antigen-specific tolerance for the treatment of ongoing, relapsing autoimmune encephalomyelitis: a comparison between oral and peripheral tolerance," J. Immunol. 159(2):1036-1044 (1997).

Kim et al., Albumin-Coated Porous Hollow Poly(Lactic-co-Glycolic Acid) Microparticles Bound with Palmityl-Acylated Exendin-4

(56) References Cited

OTHER PUBLICATIONS as a Long-Acting Inhalation Delivery System for the Treatment of Diabetes, Pharm. Res. 28:2008-2019 (2011).

Kim, et al. "Suppression of Collagen-Induced Arthritis by Single Administration of Poly(Lactic-Co-Glycolic Acid) Nanoparticles Entrapping Type II Collagen," Arthritis & Rheumatism vol. 46(4), Apr. 2002, pp. 1109-1120.

Lamprecht et al., "Biodegradable Nanoparticles for Targeted Drug Delivery in Treatment of Inflammatory Bowel Disease," J. Pharmacol. Exp. Therapeutics 299(2):775-781 (2001).

Liu et al., "Biocompatible and detectable carboxylated nanodiamond on human cell," Nanotechnol. 18(32):325102, 10 pages (2007).

Makadia, et al., Poly Lactic-co-Glycolic Acid (PLGA) as Biodegradable Controlled Drug Delivery Carrier, Polymers, 3:1377-1397, 2011.

Marazeuela et al., "Intranasal vaccination with poly(lactide-co-glycolide) microparticles containing a peptide T of Ole e 1 prevents mice against sensitization", Clinical and Experimental Allergy, vol. 38, 2008, pp. 520-528.

Merodio, et al. Distribution of albumin nanoparticles in animals induced with the experimental allergic encephalomyelitis. J Drug Target. 2000;8(5):289-303.

Nakajima et al., "Mechanism of amide formation by carbodiimide for bioconjugation in aqueous media," Bioconj. Chem. 6:123-130 (1995).

Nygaard et al. "The Allergy Adjuvant Effect of Particles—Genetic Factors Influence Antibody and Cytokine Responses." BMC Immunology. Jun. 21, 2005, vol. 6:11, pp. 1-10.

Park, Degradation of poly(lactic-co-glycolic acid) microspheres: effect of copolymer composition, Biomaterials, 16(15):1123-30 (Oct. 1995).

Pecquet et al. "Oral tolerance elicited in mice by b-lactoglobulin entrapped in biodegradable microspheres," Vaccine 2000 vol. 18: 1196-1202.

Sahoo et al., "Residual polyvinyl alcohol associated with poly (D,L-lactide-co-glycolide) nanoparticels affects their physical properties and cellular uptake," J. Control. Rel. 82:105114 (2002).

Saint-Lu et al., "Targeting the allergen to oral dendritic cells with mucoadhesive chitosan particles enhances tolerance induction," Allergy 64(7):1003-1013 (2009).

Supplementary European Search Report. EP appl. No. 11839890.8, 8 pages (Jun. 15, 2016).

Zolnik et al., "Minireview: Nanoparticles and the Immune System," Endocrinol. 151(2):458-465 (2010).

Nenmar et al., Inflammatory effect of intratracheal instillation of ultrafine particles in the rabbit: role of C-fiber and mast cells, Toxicol. Appl. Pharmacol., 160(3):250-61 (Nov. 1999).

"Subcutaneous Administration", pp. 5-8 IN: Goodman & Gilman's the Pharmacological Basis of Therapeutics, Ninth Edition, McGraw-Hill (1996).

Kupffer et al., Kupffer cell-mediated hepatic injury induced by silica nanoparticles in vitro and in vivo, Int. J. Nanomedicine, 8:1129-40 (2013).

Yazdi et al., Nanoparticles activate the NLR pyrin domain containing 3 (Nlrp3) inflammasome and cause pulmonary inflammation through release of IL-1a and IL-1β, Proc. Natl. Acad. Sci. USA, 107(45):19449-54 (Nov. 2010).

Frasnelli et al., TLR2 modulates inflammation in zymosan-induced arthritis in mice, Arthritis Res. Ther., 7(2):R370-9 (2005).

Hunter et al., A biodegradable nanoparticle platform for the induction of antigen-specific immune tolerance for treatment of autoimmune disease, ACS Nano, 8(3):2148-60 (Mar. 2014).

Brandenberger et al., Engineered silica nanoparticles act as adjuvants to enhance allergic airway disease in mice, Part Fibre Toxicol., 10:26 (Jul. 2013).

Wooley et al., Inflammatory responses to orthopaedic biomaterials in the murine air pouch, Biomateials, 23(2):517-26 (Jan. 2002).

\* cited by examiner

FIGURE 1

FIGURE 5
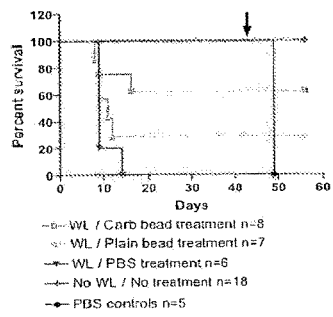
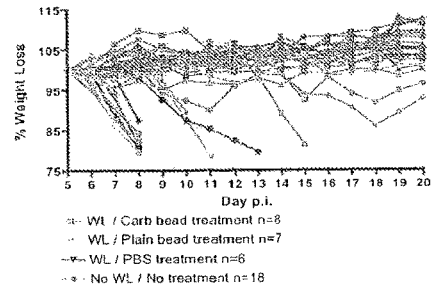
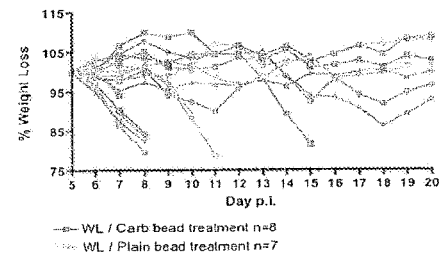
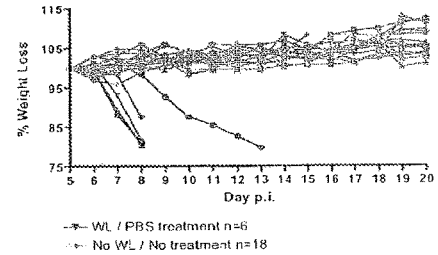
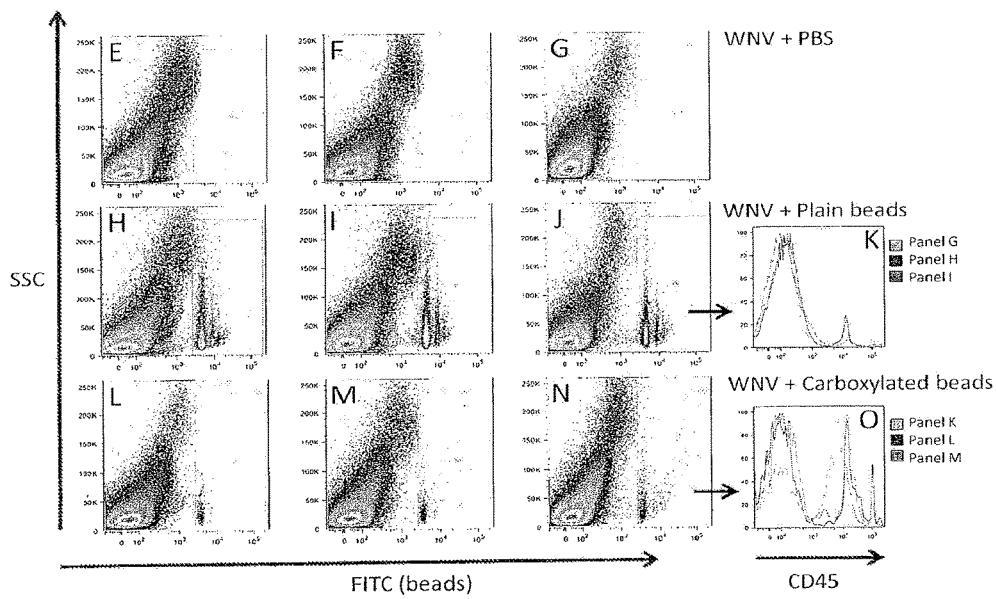

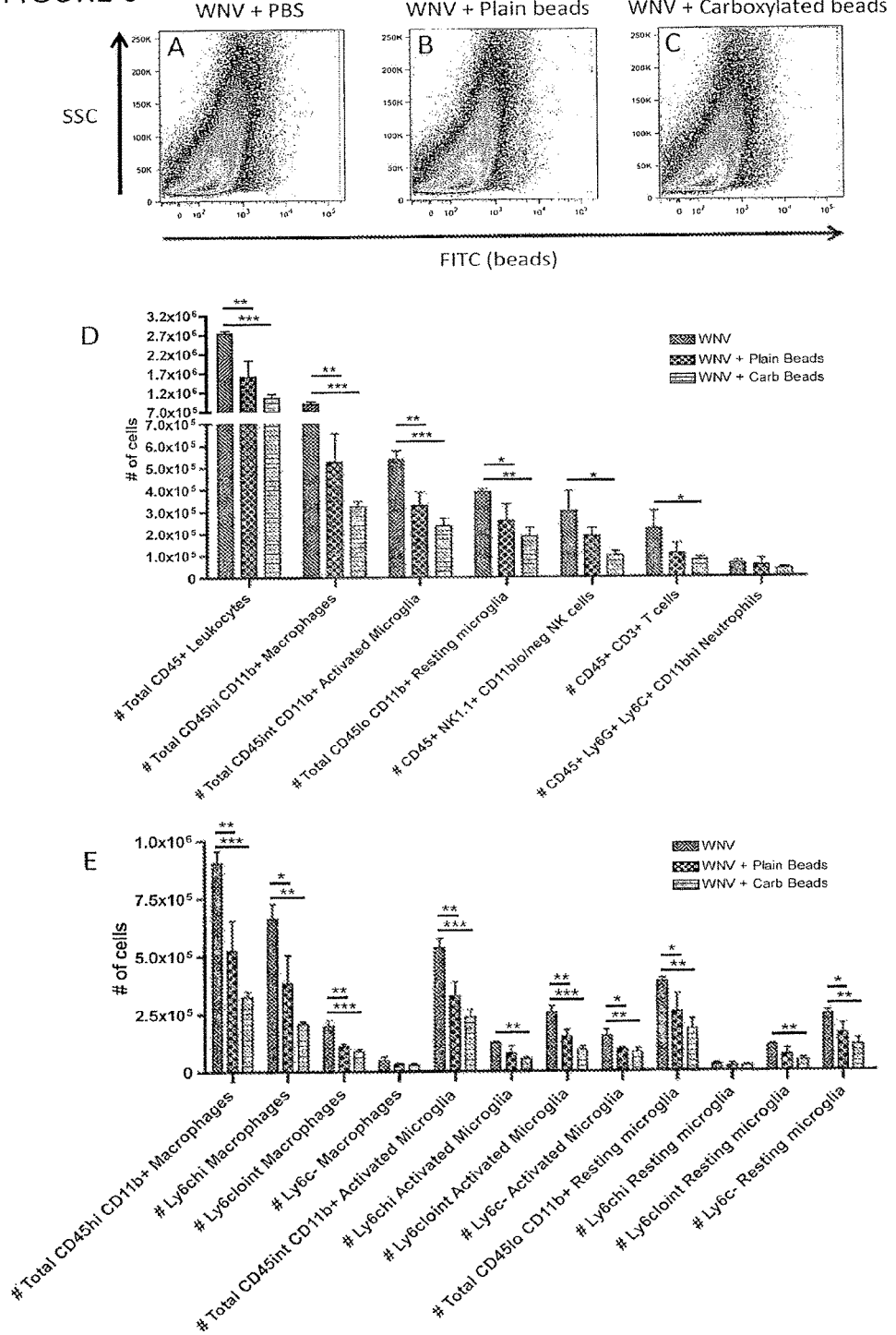

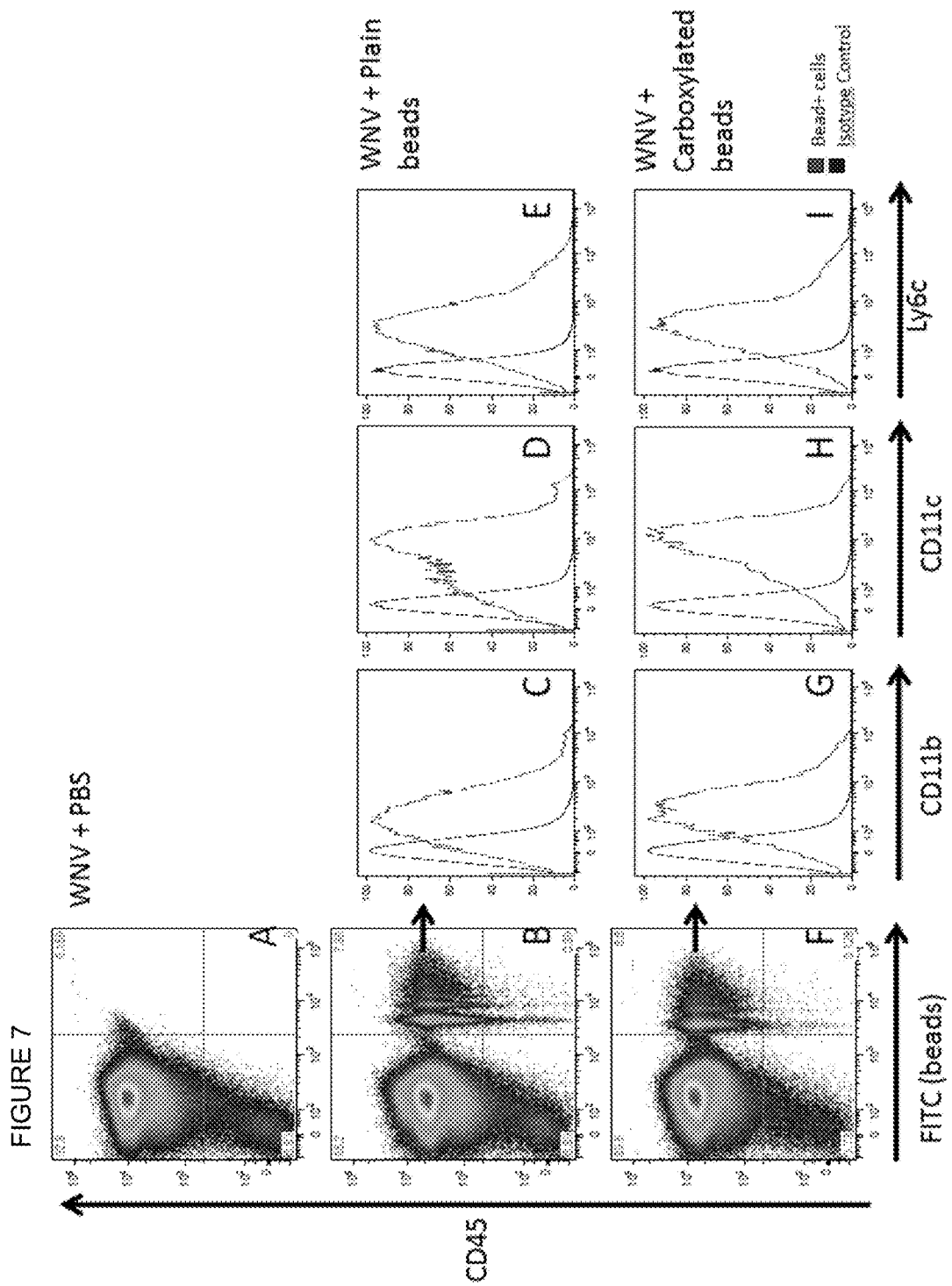

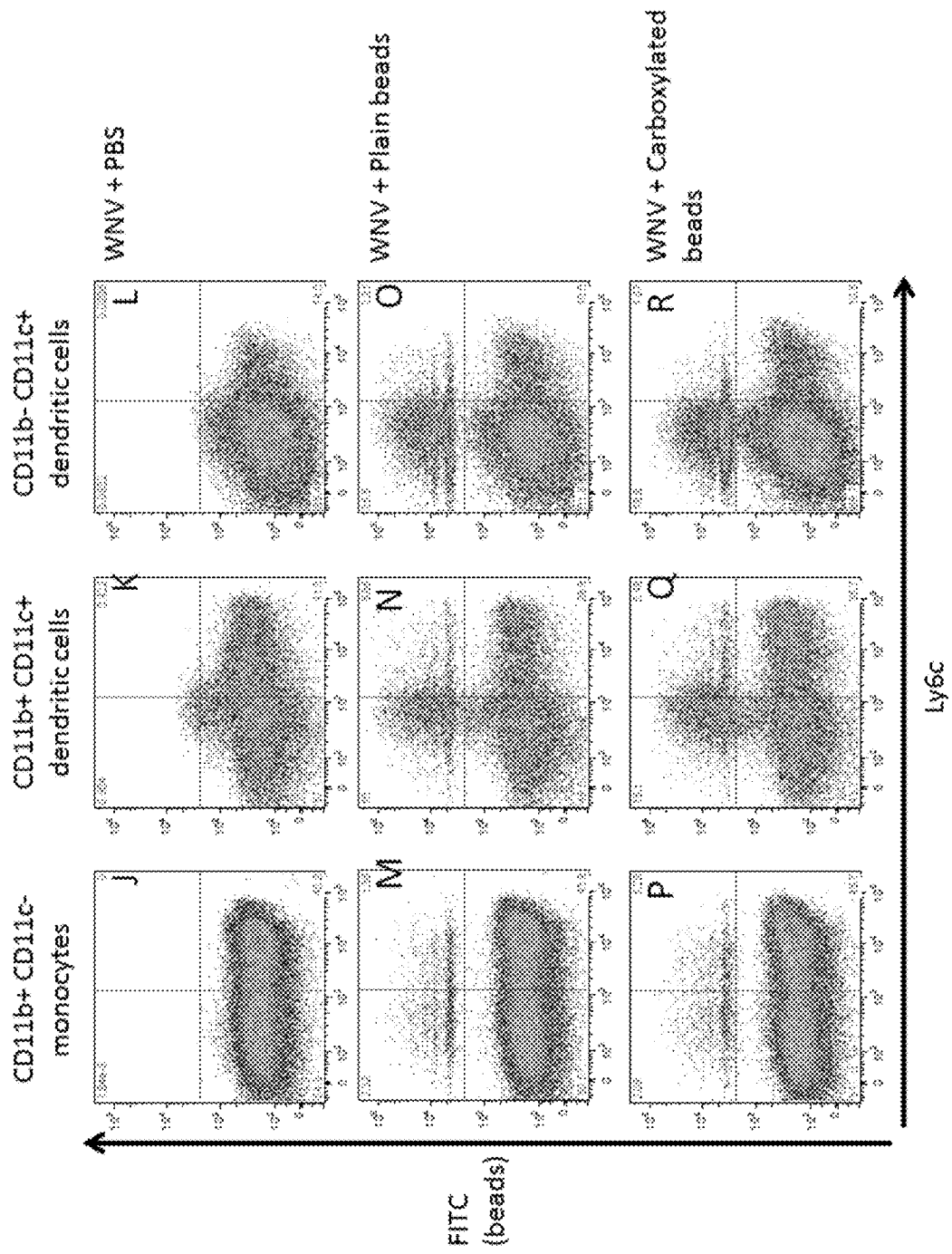

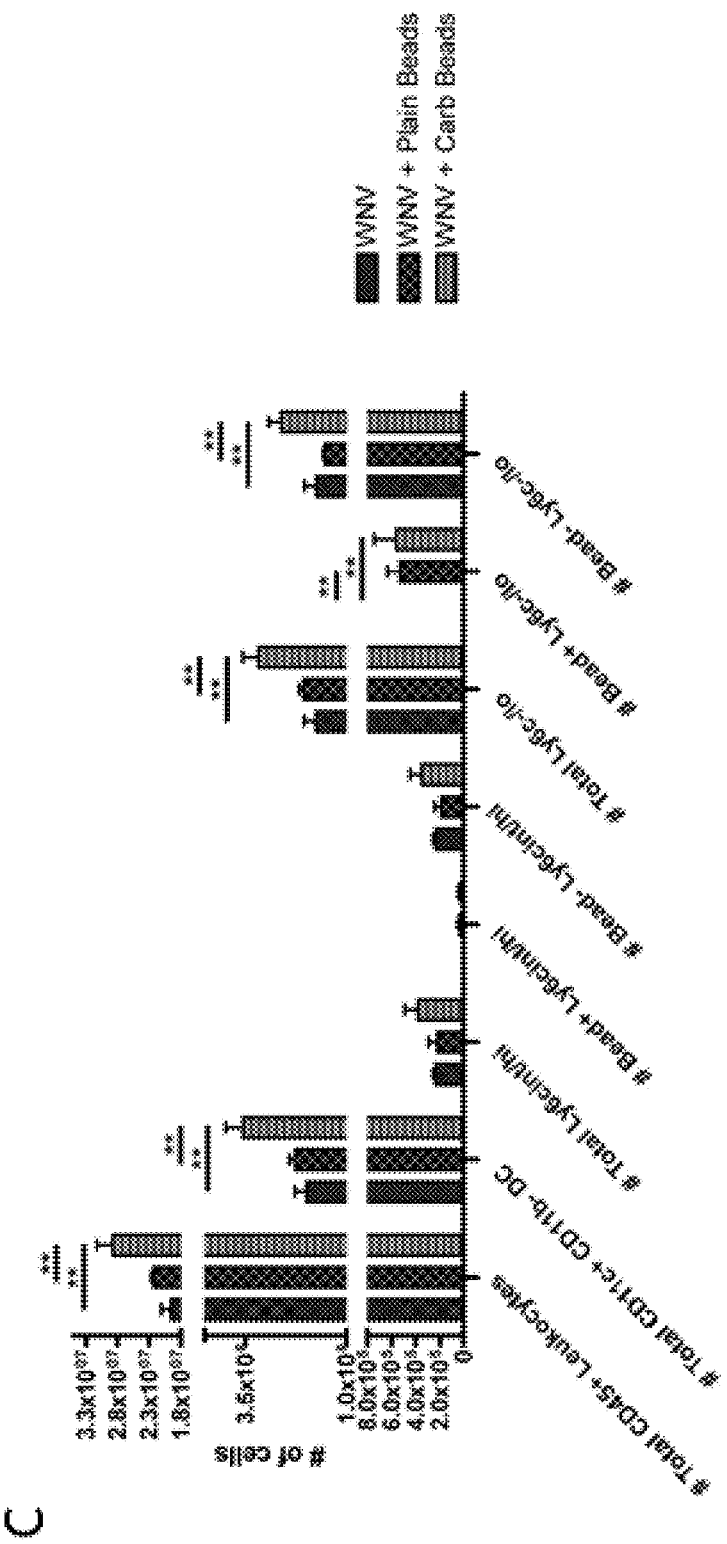

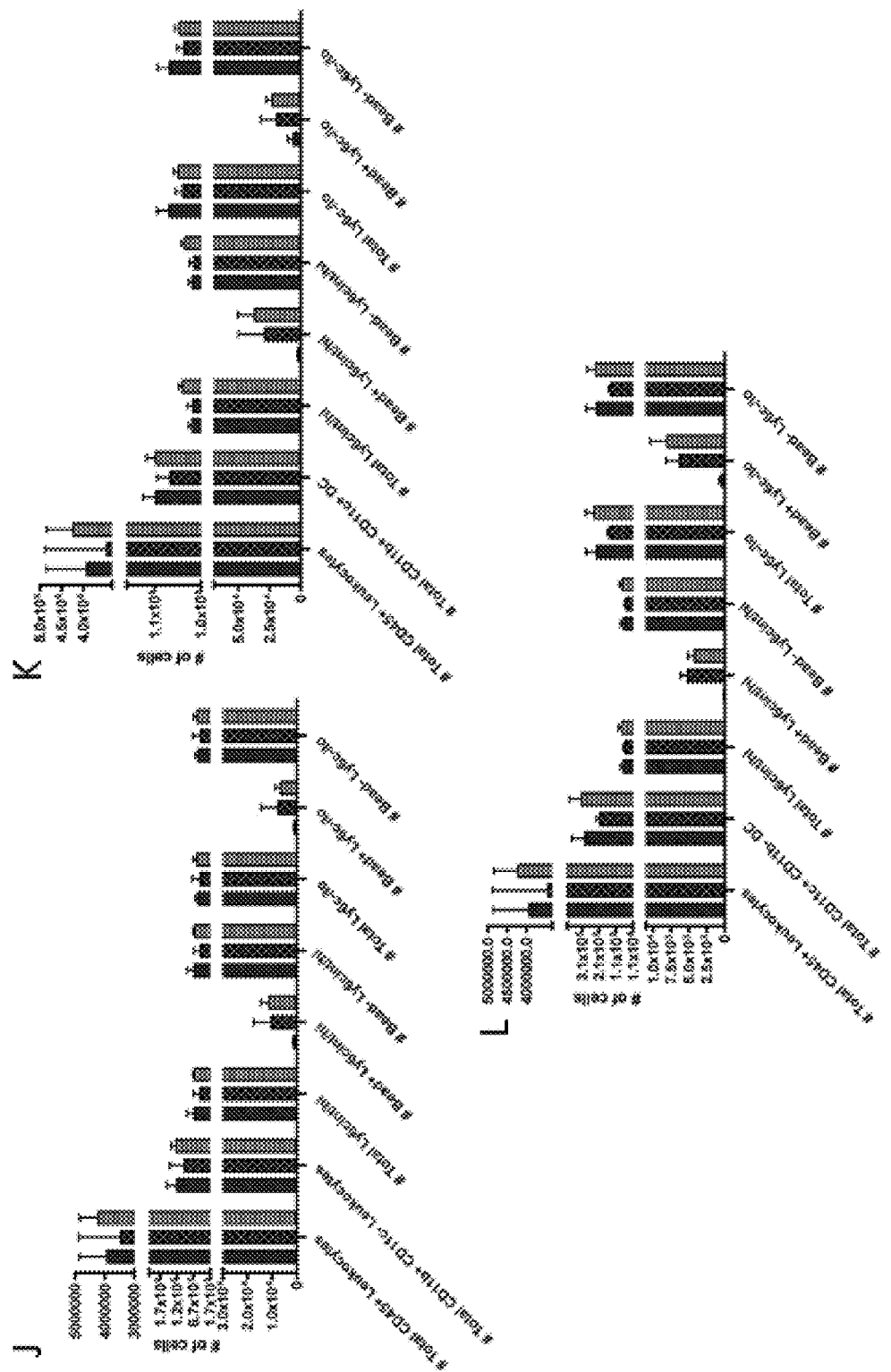
FIGURE 10 CON'T

MODIFIED IMMUNE-MODULATING PARTICLES

CROSS REFERENCE TO RELATED APPLICATIONS

This application is a continuation of U.S. application Ser. No. 13/884,817 filed on Aug. 27, 2013, which is a national stage filing of PCT/US2011/060537, filed on Nov. 14, 2011, which claims priority to U.S. Provisional Application Nos. 61/413,016 and 61/413,018, both filed Nov. 12, 2010, each of which are incorporated by reference herein in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GETT_001_02US_SeqList_ST25.txt, date recorded: Feb. 17, 2015, file size 1 kilobyte).

BACKGROUND OF INVENTION

Inflammatory diseases and disorders are conditions in which an abnormal or otherwise deregulated inflammatory response contributes to the etiology or severity of disease. Examples include autoimmune diseases such as rheumatoid arthritis, multiple sclerosis, and diabetes, infectious diseases such as tuberculosis and various forms of meningitis and encephalitis including West Nile Virus encephalitis and other disorders include atherosclerosis and ischemic reperfusion.

Many of these diseases are characterized by a mononuclear cell infiltration at a site of tissue injury or other insult. Examples of mononuclear cells that have been observed in these infiltrations include lymphocytes, especially T lymphocytes, and cells of the mononuclear phagocyte system (MPS cells) such as monocytes, macrophages, dendritic cells, microglial cells and others.

Many of the cells observed in the mononuclear cell infiltrates are suspected of having a role in these abnormal inflammatory responses. For example, in diseases such as multiple sclerosis, CD4$^1$ T cells are known to play a central role in the pathologic autoimmune response. At an earlier time point in T cell activation, dendritic cells and other MPS cells may be responsible for activation of CD4$^+$ T cells. MPS cells could also contribute to inflammation through phagocytosis although in at least some inflammatory diseases it is not clear whether such cells would be capable of this in the absence of CD4$^+$ T cells.

Peripheral blood monocytes may be classified into one of two groups according to the expression or not of certain cell surface molecules. In particular, human "resident monocytes" or "mature monocytes" are understood to have a CD14$^{lo}$CD16$^+$ phenotype (the mouse counterpart is CX$_3$CR1$^{hi}$CCR2$^-$Gr1$^-$). Another group of cells, the "inflammatory monocytes" or "immature monocytes" are understood to have a CD14$^+$CD16$^-$ phenotype (the mouse counterpart is CX$_3$CR1$^{lo}$CCR2$^+$Gr1$^+$). (Geissmann F. et al. 2003 Immunity 19: 71-82)

Importantly, while the latter are understood to be "inflammatory" in the sense that they are observed to migrate into inflamed tissue from bone marrow derived peripheral blood cells, these cells have not been shown to cause inflammation either directly or through the action of other cells. Further, the various MPS cells that may be formed when these cells differentiate have also not been shown to cause inflammation.

Conventional clinical strategies for general long-term immunosuppression in disorders associated with an undesired immune response are based on the long-term administration of broad acting immunosuppressive drugs, for example, signal 1 blockers such as cyclosporin A (CsA), FK506 (tacrolimus) and corticosteroids. Long-term use of high doses of these drugs can have toxic side-effects. Moreover, even in those patients that are able to tolerate these drugs, the requirement for life-long immunosuppressive drug therapy carries a significant risk of severe side effects, including tumors, serious infections, nephrotoxicity and metabolic disorders.

Methods of inducing antigen-specific tolerance have been developed, including cell coupling of an antigen or peptide. For example, in one method, peptide induced cell coupled tolerance involved collection, separation and treatment of peripheral blood cells with disease specific autoantigens and the ethylene carbodimide (ECDI) coupling reagent under sterile conditions, and subsequent re-infusion into the donor/patient. This process is costly and must be conducted under closely monitored conditions by skilled practitioners and is limited in the number of centers that can conduct the procedure The use of red blood cells as the donor cell type expands the potential source to include allogeneic donors thus increasing the supply of source cells dramatically and potentially expanding the delivery of this therapy to any setting certified for blood transfusion. These approaches have significant limitations in terms of supply of source cells and necessity for tissue type matching to minimize immune response to the donor cells. In addition the local treatment of the cells to couple autoantigens via EDCI presents a significant quality control issue. Furthermore, these approaches also require at least some knowledge of the pathological antigen for which immune tolerance is sought.

Recently, peptide-coupled particles have been described which eliminates the requirement for a supply of source cells and circumvents the tissue-typing requirement of the prior approaches, See WO 2010/085509, incorporated by reference herein in its entirety. However, these approaches still rely on antigen-specific immune tolerance.

Antigen-specific tolerance is generally not ideal because specific antigens/epitopes are generally not known in human diseases. Furthermore, antigens can vary from subject to subject in order for an antigen specific approach to be effective, therefore it would be necessary to determine which antigens each individual patient would recognize, or it would require coupling a library of possible peptides to the particles prior to administration. The synthesis and individual coupling of these peptides is both time consuming and expensive. Therefore, a need exists for a therapy which solves both of these problems thereby eliminating the need to for a source of tissue matched cells and at the same time eliminating the need to synthesize and couple large panels of peptides.

SUMMARY OF THE INVENTION

The current invention involves the surprising finding that modified particles alone, that is, without a peptide coupled thereto, are effective in ameliorating the inflammatory immune response in patients in need thereof. Surprisingly, all that is necessary to dampen an inflammatory immune response, and treat inflammatory disease is the administration of carboxylated particles, without the need for coupling peptide(s) thereto.

In a one embodiment, the current invention provides a pharmaceutical composition comprising carboxylated particles. In a further embodiment, the carboxylated particles are free from attached peptide or antigenic moieties. In some embodiments, the carboxylated particles are polystyrene particles. In other embodiments, the carboxylated particles are diamond particles. In still other embodiments, the carboxylated particles are poly(lactic-co-glycolic acid) (PLGA) particles.

In one embodiment, the pharmaceutical composition containing the carboxylated particles induces immune tolerance when administered to a subject in need thereof. In a further embodiment, the pharmaceutical composition containing the carboxylated particles ameliorates an inflammatory immune response when administered to a subject in need thereof.

In one embodiment, the carboxylated particles comprising the pharmaceutical formulation of the current invention have a diameter of about 0.1 µm to about 10 µm. In a further embodiment, the carboxylated particles have a diameter of about 0.3 µm to about 5 µm. In yet a further embodiment the carboxylated particles have a diameter of about 0.5 µm to about 3 µm. In still a further embodiment, the carboxylated particles have a diameter of about 0.5 µm.

In one embodiment, the current invention provides a method of reducing the duration or severity of an inflammatory immune response in a subject comprising administering to the subject a pharmaceutical composition comprising carboxylated particles. In a further embodiment, the carboxylated particles are free from attached peptide or antigenic moieties. In some embodiments, the carboxylated particles are polystyrene particles. In other embodiments, the carboxylated particles are diamond particles. In still other embodiments, the carboxylated particles are poly(lactic-co-glycolic acid) (PLGA) particles.

In one embodiment, the method of the invention induces immune tolerance when administered to a subject in need thereof. In a further embodiment, the method ameliorates an inflammatory immune response when administered to a subject in need thereof.

In one embodiment, the method of the invention utilizes carboxylated particles comprising those having a diameter of about 0.1 µm to about 10 µm. In a further embodiment, the carboxylated particles have a diameter of about 0.3 µm to about 5 µm. In yet a further embodiment the carboxylated particles have a diameter of about 0.5 µm to about 3 µm. In still a further embodiment, the carboxylated particles have a diameter of about 0.5 µm.

In one embodiment, the subject has an autoimmune disorder. In a further embodiment the autoimmune disorder is multiple sclerosis, scleroderma, type-I diabetes, rheumatoid arthritis, thyroiditis, systemic lupus erythematosis, Reynauud's syndrome, Sjorgen's syndrome, autoimmune uveitis, autoimmune myocarditis, or Crohn's disease. In a particular embodiment, the autoimmune disease is multiple sclerosis In another embodiment, the subject has an allergic disorder. In a further embodiment, the allergic disorder is eczema, asthma, allergic rhinitis or skin hypersensitivity.

In another embodiment, the subject is a transplant recipient. In still another embodiment, the subject has suffered a cardiac infarction. In still another embodiment, the patient has ischemic reperfusion. In still another embodiment, the patient has atherosclerosis.

In one embodiment, the method includes administering the carboxylated particles by any suitable means. In one embodiment, the composition is administered orally, nasally, intravenously, intramuscularly, ocularly, transdermally, or subcutaneously. In a particular embodiment, the carboxylated particles are administered nasally. In still another embodiment, the particles are administered intravenously.

In one embodiment, the current invention provides a method of treating a bacterial or viral infection in a subject comprising administering to the subject a pharmaceutical composition comprising carboxylated particles. In a further embodiment, the carboxylated particles are free from attached peptide or antigenic moieties. In some embodiments, the carboxylated particles are polystyrene particles. In other embodiments, the carboxylated particles are diamond particles. In still other embodiments, the carboxylated particles are poly(lactic-co-glycolic acid) (PLGA) particles.

In one embodiment, the method of the invention induces immune tolerance when administered to a subject with a bacterial or viral infection. In a further embodiment, the method ameliorates or dampens an inflammatory immune response when administered to a subject with a bacterial or viral infection.

In one embodiment, the methods of treating a bacterial or viral infection of the invention utilizes carboxylated particles comprising having a diameter of about 0.1 µm to about 10 µm. In a further embodiment, the carboxylated particles have a diameter of about 0.3 µm to about 5 µm. In yet a further embodiment the carboxylated particles have a diameter of about 0.5 µm to about 3 µm. In still a further embodiment, the carboxylated particles have a diameter of about 0.5 µm.

In one embodiment, the subject has a viral infection. In a further embodiment, the viral infection is a herpes virus infection, a hepatitis virus infection, a west nile virus infection, a flavivirus, an influenza infection, a rhinovirus infection, a papillomavirus infection, a or parainfluenza virus infection. In a further embodiment, the viral infection infects the central nervous system of said subject. In still a further embodiment, the viral infection causes viral encephalitis or viral meningitis.

In one embodiment, the subject has a bacterial infection. In a further embodiment, the bacterial infection infects the central nervous system of said subject. In still a further embodiment, the bacterial infection causes sepsis bacterial encephalitis or bacterial meningitis.

BRIEF DESCRIPTION OF THE DRAWINGS

FIG. 1 shows (A) the percent survival of mice after high dose or low dose infection with WNV; (B) weight loss associated with high dose infection of mice with WN V; (C) the viral titers in the brain of mice that succumb to infection; (D) weight loss in mice infected with high and low dose WNV through days 0-7 post infection; (E) the viral titers in the brains of mice infected with high and low dose WNV at day 7 post infection and the correlation between percentage of weight loss on day 7 and viral titer; (F) the correlation between percentage weight loss and the presence of $CD45^+$ leukocytes in the brain of mice at 7 days post infection with high and low dose WN V; (G) the correlation between viral titer in the brain and the presence of $CD45^+$ leukocytes in the brain of mice at 7 days post infection with high and low dose WNV; (H) the correlation between percentage weight loss and the presence of $CD45^{hi}$ macrophages in the brain of mice at 7 days post infection with high and low dose WNV.

FIG. 5 shows (A) the difference in survival of mice treated with carboxylated polystyrene beads, naked polystyrene beads or PBS after low dose infection with WN V; (B) shows the difference in percent weight loss in mice treated with carboxylated beads, naked beads or PBS after low dose infection with WNV; (C,D) shows the difference in percent weight loss between carboxylated bead treatment and naked bead treatment in mice after low dose infection with WNV; (E,O) shows the localization of FITC-conjugated carboxylated beads or naked beads on day 7 in mice infected with high dose WNV on day 0 and FITC-carboxylated beads, FITC-naked beads or PBS on day 6. (E-G) are blood from 3 separate PBS-treated mice, (H-J) are blood from 3 separate naked polystyrene bead-treated mice, and (L-N) are blood from 3 separate carboxylated polystyrene bead-treated mice, showing that more of the plain beads remain in the blood than carboxylated beads.

FIG. 6 shows (A-C) the lack of infiltration of FITC-conjugated polystyrene beads in the brains of mice infected and treated as in Figure E-O; (D-E) shows the reduction in infiltration of various leukocytes, macrophages and microglia into the brains of WNV-infected mice treated with carboxylated polystyrene beads or naked polystyrene beads as in FIG. 5 (E-O).

FIG. 7 shows (A) the association of FITC-conjugated polystyrene carboxylated beads and FITC-conjugated naked polystyrene beads in the spleen with CD45$^+$ leukocytes (A,B,F) within CD11b$^+$ (C,G), CD11c$^+$ (D,H) Ly6c$^+$ (E,I) cells; (J-R) shows the types of cells that take up FITC-conjugated carboxylated beads and FITC-conjugated naked beads

DETAILED DESCRIPTION OF THE INVENTION

Figure 2:
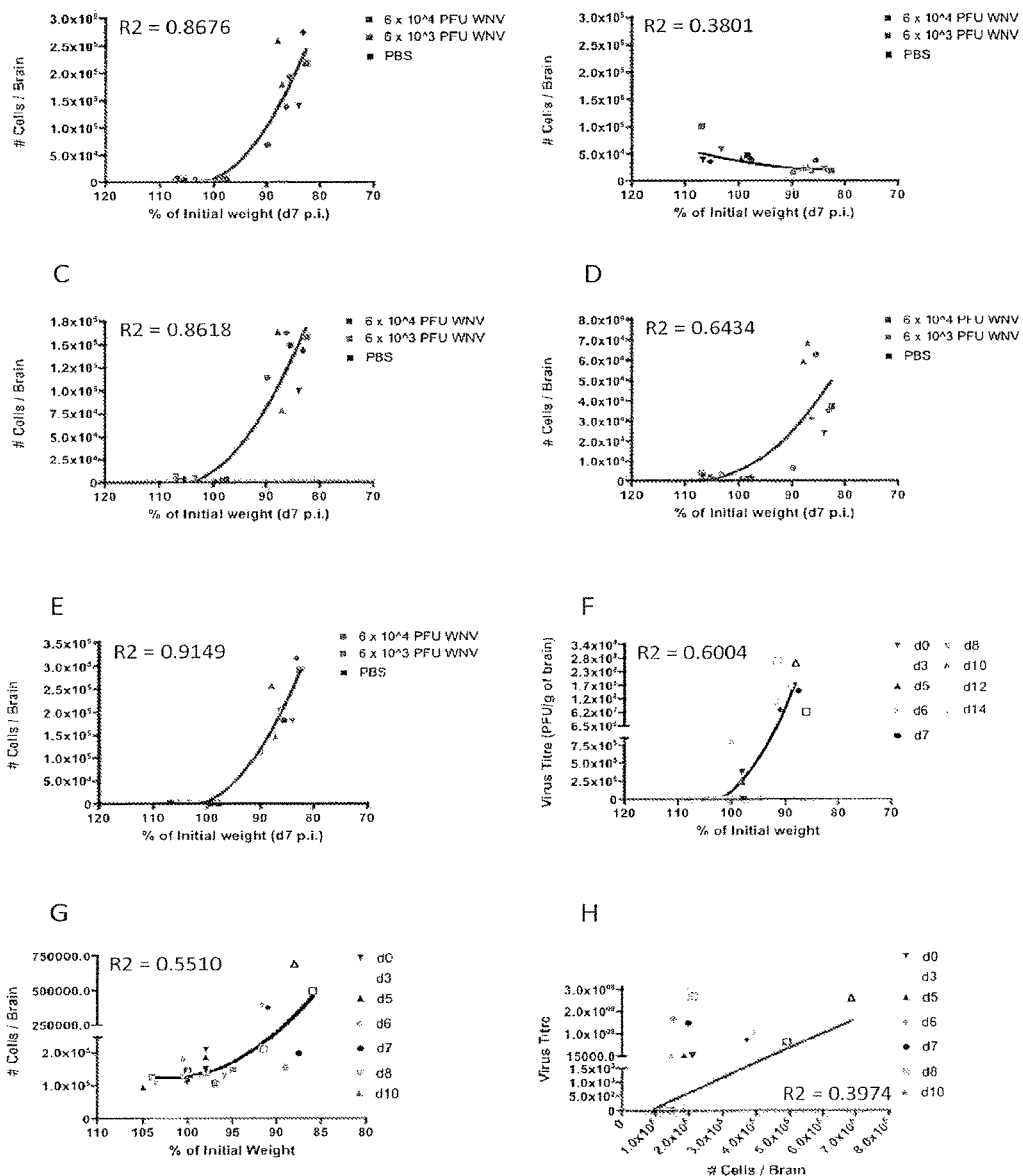
FIG. 2 shows the correlation between percentage of weight loss and the presence of (A) CD45$^{int}$CD11b$^+$ immigrant microglia; (C) CD3$^+$ T cells; (D) CD11b$^{hi}$ Ly6G$^+$ neutrophils and (E) NK1.1$^+$CD11b$^{lo/-}$ natural killer cells while the numbers of CD45$^{lo}$ resident microglia (B) remained unchanged after 7 days post infection with high dose or low dose WNV; (F) shows the correlation between weight loss and virus titer in the brain at the time of sacrifice of mice infected with low dose WNV; (G) shows the correlation of leukocyte infiltration and percentage weight loss in mice infected with low dose WNV and (H) shows that there was no correlation between virus titer and leukocyte infiltration after low dose WNV infection.

The present inventors have surprisingly found that when carboxylated particles, such as carboxylated polystyrene, PLGA, or diamond particles of a certain size, are administered to subjects, inflammatory immune responses are ameliorated. Additionally, the present inventors have also surprisingly found that these same carboxylated particles, when administered to subjects with active viral or bacterial infections, particularly those infecting the central nervous system prolong, lead to a dramatic decrease in symptoms of these infections and prolonged survival. These, particles, therefore, may be useful in the treatment of any disease or condition characterized by an excessive inflammatory immune response, such as autoimmune diseases, as well as in the treatment of bacterial and viral infections.

"Particle" as used herein refer to any non-tissue derived minute composition of matter, it may be a sphere or sphere-like entity or bead. The term "particle" and the term "bead" may be used interchangeably. Additionally, the term "particle" may be used to encompass beads and spheres.

"Carboxylated particles" or "carboxylated beads" or "carboxylated spheres" includes any particle that has been modified to contain a carboxyl group on its surface. In some embodiments the addition of the carboxyl group enhances phagocyte/monocyte uptake of the particles from circulation, for instance through the interaction with scavenger receptors such as MARCO.

"Antigenic moiety" as used herein refers to any moiety, for example a peptide, that is recognized by the host's immune system. Examples of antigenic moieties include, but are not limited to, autoantigens and/or bacterial or viral proteins, peptides or components. Without being bound by theory, while the carboxylated beads themselves may be recognized by the immune system, the carboxylated beads with nothing more attached thereto are not considered an "antigenic moiety" for the purposes of the invention.

"Naked beads" or "naked particles" or "naked spheres" as used herein refers to beads, particles or spheres that have not been carboxylated.

The particle may have any particle shape or conformation. However, in some embodiments it is preferred to use particles that are less likely to clump in vivo. Examples of particles within these embodiments are those that have a spherical shape.

It is not necessary that each particle be uniform in size, although the particles must generally be of a size sufficient to trigger phagocytosis in an antigen presenting cell or other MPS cell. Preferable, the particles are microscopic or nanoscopic in size, in order to enhance solubility, avoid possible complications caused by aggregation in vivo and to facilitate pinocytosis. Particle size can be a factor for uptake from the interstitial space into areas of lymphocyte maturation. A particle having a diameter of from about 0.1 µm to about 10 µm is capable of triggering phagocytosis. Thus in one embodiment, the particle has a diameter within these limits. In another embodiment, the particle has a diameter of about 0.3 µm to about 5 µm. In still another embodiment, the particle has a diameter of about 0.5 µm to about 3 µm. In preferred embodiment the particle has a size of about 0.5 µm. The particles in a composition need not be of uniform diameter. By way of example, a pharmaceutical formulation may contain a plurality of particles, some of which are about 0.5 µm, while others are about 1.0 µm. Any mixture of particle sizes within these given ranges will be useful.

In some embodiments, the particle is non-metallic. In these embodiments the particle may be formed from a polymer. In a preferred embodiment, the particle is biodegradable in an individual. In this embodiment, the particles can be provided to an individual across multiple doses without there being an accumulation of particles in the individual. Examples of suitable particles include polystyrene particles, PLGA particles, and diamond particles.

Preferably the particle surface is composed of a material that minimizes non-specific or unwanted biological interactions. Interactions between the particle surface and the interstitium may be a factor that plays a role in lymphatic uptake. The particle surface may be coated with a material to prevent or decrease non-specific interactions. Steric stabilization by coating particles with hydrophilic layers such as poly(ethylene glycol) (PEG) and its copolymers such as PLURONICS (including copolymers of poly(ethylene glycol)-bl-poly(propylene glycol)-bl-poly(ethylene glycol)) may reduce the non-specific interactions with proteins of the interstitium as demonstrated by improved lymphatic uptake following subcutaneous injections. All of these facts point to the significance of the physical properties of the particles in terms of lymphatic uptake. Biodegradable polymers may be used to make all or some of the polymers and/or particles and/or layers. Biodegradable polymers may undergo degradation, for example, by a result of functional groups reacting with the water in the solution. The term "degradation" as used herein refers to becoming soluble, either by reduction of molecular weight or by conversion of hydrophobic groups to hydrophilic groups. Polymers with ester groups are generally subject to spontaneous hydrolysis, e.g., polylactides and polyglycolides.

Particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez, et al., Science, 1998, 281, 2013; Niemeyer, C. M Angew. Chem. Int. Ed. 2003, 42, 5796; Waggoner, A. Methods Enzymol. 1995, 246, 362; Brus, L. E. J. Chem. Phys. 1993, 79, 5566). Quantum dots, such as hybrid organic/inorganic quantum dots based on a class of polymers known as dendrimers, may used in biological labeling, imaging, and optical biosensing systems. (Lemon, et al., J. Am. Chem. Soc. 2000, 122, 12886). Unlike the traditional synthesis of inorganic quantum dots, the synthesis of these hybrid quantum dot nanoparticles does not require high temperatures or highly toxic, unstable reagents. (Etienne, et al., Appl. Phys. Lett. 87, 181913, 2005).

Particles can be formed from a wide range of materials. The particle is preferably composed of a material suitable for biological use. For example, particles may be composed of glass, silica, polyesters of hydroxy carboxylic acids, polyanhydrides of dicarboxylic acids, or copolymers of hydroxy carboxylic acids and dicarboxylic acids. More generally, the carrier particles may be composed of polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids, or polyanhydrides of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy dicarboxylic acids. Additionally, carrier particles can be quantum dots, or composed of quantum dots, such as quantum dot polystyrene particles (Joumaa et al. (2006) Langmuir 22: 1810-6). Carrier particles including mixtures of ester and anhydride bonds (e.g., copolymers of glycolic and sebacic acid) may also be employed. For example, carrier particles may comprise materials including polyglycolic acid polymers (PGA), polylactic acid polymers (PLA), polysebacic acid polymers (PSA), poly(lactic-co-glycolic) acid copolymers (PLGA), [rho]oly(lactic-co-sebacic) acid copolymers (PLSA), poly (glycolic-co-sebacic) acid copolymers (PGSA), etc. Other biocompatible, biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or dicarboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials to provide reactive groups for conjugating to antigen peptides and proteins or conjugating moieties. Biodegradable materials suitable for the present invention include diamond, PLA, PGA, and PLGA polymers. Biocompatible but non-biodegradable materials may also be used in the carrier particles of the invention. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons may be employed.

Suitable beads which are currently available commercially include polystyrene beads such as FluoSpheres (Molecular Probes, Eugene, Oreg.).

Physical properties are also related to a nanoparticle's usefulness after uptake and retention in areas having immature lymphocytes. These include mechanical properties such as rigidity or rubberiness. Some embodiments are based on a rubbery core, e.g., a poly(propylene sulfide) (PPS) core with an overlayer, e.g., a hydrophilic overlayer, as in PEG, as in the PPS-PEG system recently developed and characterized for systemic (but not targeted or immune) delivery. The rubbery core is in contrast to a substantially rigid core as in a polystyrene or metal nanoparticle system. The term rubbery refers to certain resilient materials besides natural or synthetic rubbers, with rubbery being a term familiar to those in the polymer arts. For example, cross-linked PPS can be used to form a hydrophobic rubbery core. PPS is a polymer that degrades under oxidative conditions to polysulphoxide and finally polysulphone, transitioning from a hydrophobic rubber to a hydrophilic, water-soluble polymer. Other sulphide polymers may be adapted for use, with the term sulphide polymer referring to a polymer with a sulphur in the backbone of the mer. Other rubbery polymers that may be used are polyesters with glass transition temperature under hydrated conditions that is less than about 37° C. A hydrophobic core can be advantageously used with a hydrophilic overlayer since the core and overlayer will tend not to mingle, so that the overlayer tends to sterically expand away from the core. A core refers to a particle that has a layer on it. A layer refers to a material covering at least a portion of the core. A layer may be adsorbed or covalently bound. A particle or core may be solid or hollow. Rubbery hydrophobic cores are advantageous over rigid hydrophobic cores, such as crystalline or glassy (as in the case of polystyrene) cores, in that higher loadings of hydrophobic drugs can be carried by the particles with the rubbery hydrophobic cores.

Another physical property is the surface's hydrophilicity. A hydrophilic material may have a solubility in water of at least 1 gram per liter when it is uncrosslinked. Steric stabilization of particles with hydrophilic polymers can improve uptake from the interstitium by reducing non-specific interactions; however, the particles' increased stealth nature can also reduce internalization by phagocytic cells in areas having immature lymphocytes. The challenge of balancing these competing features has been met, however, and this application documents the creation of nanoparticles for effective lymphatic delivery to DCs and other APCs in lymph nodes. Some embodiments include a hydrophilic component, e.g., a layer of hydrophilic material. Examples of suitable hydrophilic materials are one or more of polyalkylene oxides, polyethylene oxides, polysaccharides, polyacrylic acids, and polyethers. The molecular weight of polymers in a layer can be adjusted to provide a useful degree of steric hindrance in vivo, e.g., from about 1,000 to about 100,000 or even more; artisans will immediately appreciate that all the ranges and values within the explicitly stated ranges are contemplated, e.g., between 10,000 and 50,000.

The nanoparticles may incorporate functional groups for further reaction. Functional groups for further reaction include electrophiles or nucleophiles; these are convenient for reacting with other molecules. Examples of nucleophiles are primary amines, thiols, and hydroxyls. Examples of electrophiles are succinimidyl esters, aldehydes, isocyanates, and maleimides.

The particles of the current invention can be given in any dose effective to dampen the inflammatory immune response in a subject in need thereof or to treat a bacterial or viral infection in a subject in need thereof. In certain embodiments, about $10^2$ to about $10^{20}$ particles are provided to the individual. In a further embodiment between about $10^3$ to about $10^{15}$ particles are provided. In yet a further embodiment, between about $10^6$ to about $10^{12}$ particles are provided. In still a further embodiment between about $10^8$ to about $10^{10}$ particles are provided. In one embodiment the preferred dose is 0.1% solids/ml. Therefore, for 0.5 μm beads, a preferred dose is approximately $4 \times 10^9$ beads, for 0.05 μm beads, a preferred dose is approximately $4 \times 10^{12}$ beads, for 3 μm beads, a preferred dose is $2 \times 10^7$ beads. However, any dose that is effective in treating the particular condition to be treated is encompassed by the current invention.

The invention is useful for treatment of immune related disorders such as autoimmune disease, transplant rejection and allergic reactions. Substitution of a synthetic, biocompatible particle system to induce immune tolerance could lead to ease of manufacturing, broad availability of therapeutic agents, increase uniformity between samples, increase the number of potential treatment sites and dramatically reduce the potential for allergic responses to a carrier cell.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells ($CD4^+$, $CD8^+$, Th1 and Th2 cells); antigen presenting cells (e.g., professional antigen presenting cells such as dendritic cells, macrophages, B lymphocytes, Langerhans cells, and nonprofessional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In some embodiments, the modified particles of the present invention are effective to reduce inflammatory cell trafficking to the site of inflammation.

As used herein, the term "anergy," "tolerance," or "antigen-specific tolerance" refers to insensitivity of T cells to T cell receptor-mediated stimulation. Such insensitivity is generally antigen-specific and persists after exposure to the antigenic peptide has ceased. For example, anergy in T cells is characterized by lack of cytokine production, e.g., IL-2. T-cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if re-exposure occurs in the presence of a costimulatory molecule) results in failure to produce cytokines and subsequently failure to proliferate. Thus, a failure to produce cytokines prevents proliferation. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate DL-2 gene transcription induced by a heterologous promoter under the control of the 5' IL-2 gene enhancer or by a multimer of the API sequence that can be found within the enhancer (Kang et al. 1992 Science. 257:1134).

As used herein, the term "immunological tolerance" refers to methods performed on a proportion of treated subjects in comparison with untreated subjects where: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological tolerance occurs when immunological tolerance is preferentially invoked against certain antigens in comparison with others. "Non-Specific" immunological tolerance occurs when immunological tolerance is invoked indiscriminately against antigens which lead to an inflammatory immune response. "Quasi-Specific" immunological tolerance occurs when immunological tolerance is invoked semi-discriminately against antigens which lead to a pathogenic immune response but not to others which lead to a protective immune response.

A proxy for tolerogenic activity is the ability of a particle to stimulate the production of an appropriate cytokine at the target site. The immunoregulatory cytokine released by T suppressor cells at the target site is thought to be TGF-13 (Miller et al., Proc. Natl. Acad. Sci. USA 89:421, 1992). Other factors that may be produced during tolerance are the cytokines IL-4 and IL-10, and the mediator PGE. In contrast, lymphocytes in tissues undergoing active immune destruction secrete cytokines such as IL-1, IL-2, IL-6, and IFNγ. Hence, the efficacy of a modified particle can be evaluated by measuring its ability to stimulate the appropriate type of cytokines.

With this in mind, a rapid screening test for modified particles, effective mucosal binding components, effective combinations, or effective modes and schedules of mucosal administration can be conducted using animal model systems. Animals are treated at a mucosal surface with the test particle composition, and at some time are challenged with administration of the disease causing antigen or an infectious agent. Spleen cells are isolated, and cultured in vitro in the presence of the disease causing antigen or an antigent derived from the infectious gent at a concentration of about 50 µg/mL. Cytokine secretion into the medium can be quantitated by standard immunoassay.

The ability of the particles to suppress the activity of cells can be determined using cells isolated from an animal immunized with the modified particles, or by creating a cell line responsive to a disease causing antigen or viral antigen target antigen (Ben-Nun et al., Eur. J. lmmunol. 11:195, 1981). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to coincubate within 1 mm of each other, separated by a polycarbonate membrane (WO 93/16724). In this approach, irradiation of the suppressor cell population is unnecessary, since the proliferative activity of the responders can be measured separately.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing arc included in the following section.

The invention contemplates modulation of tolerance by modulating TH1 response, TH2 response, TH17 response, or a combination of these responses. Modulating TH1 response encompasses changing expression of, e.g., interferon-gamma. Modulating TH2 response encompasses changing expression of, e.g., any combination of IL-4, IL-5, IL-10, and IL-13. Typically an increase (decrease) in TH2 response will comprise an increase (decrease) in expression of at least one of IL-4, IL-5, IL-10, or IL-13; more typically an increase (decrease) in TH2 response will comprise an increase in expression of at least two of IL-4, IL-5, IL-10, or IL-13, most typically an increase (decrease) in TH2 response will comprise an increase in at least three of IL-4, IL-5, IL-10, or IL-13, while ideally an increase (decrease) in TH2 response will comprise an increase (decrease) in expression of all of IL-4, IL-5, IL-10, and IL-13. Modulating TH17 encompasses changing expression of, e.g., TGF-beta, IL-6, IL-21 and IL-23, and effects levels of IL-17, IL-21 and IL-22.

Tolerance to autoantigens and autoimmune disease is achieved by a variety of mechanisms including negative selection of self-reactive T cells in the thymus and mechanisms of peripheral tolerance for those autoreactive T cells that escape thymic deletion and are found in the periphery. Examples of mechanisms that provide peripheral T cell tolerance include "ignorance" of self antigens, anergy or unresponsiveness to autoantigen, cytokine immune deviation, and activation-induced cell death of self-reactive T cells. In addition, regulatory T cells have been shown to be involved in mediating peripheral tolerance. See, for example, Walker et al. (2002) Nat. Rev. Immunol. 2: 11-19; Shevach et al. (2001) Immunol. Rev. 182:58-67. In some situations, peripheral tolerance to an autoantigen is lost (or broken) and an autoimmune response ensues. For example, in an animal model for EAE, activation of antigen presenting cells (APCs) through TLR innate immune receptors was shown to break self-tolerance and result in the induction of EAE (Waldner et al. (2004) J. Clin. Invest. 113:990-997).

Accordingly, in some embodiments, the invention provides methods for increasing antigen presentation while suppressing or reducing TLR7/8, TLR9, and/or TLR 7/8/9 dependent cell stimulation. As described herein, administration of particular modified particles results in antigen presentation by DCs or APCs while suppressing the TLR 7/8, TLR9, and/ot TLR7/8/9 dependent cell responses associated with immunostimulatory polynucleotides. Such suppression may include decreased levels of one or more TLR-associated cytokines.

As discussed above this invention provides novel compounds that have biological properties useful for the treatment of Mac-1 and LFA-1 mediated disorders.

Accordingly, in another aspect of the present invention, pharmaceutical compositions are provided, which comprise the carboxylated particles and optionally comprise a pharmaceutically acceptable carrier. In certain embodiments, these compositions optionally further comprise one or more additional therapeutic agents. Alternatively, the modified particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder characterized by an uncontrolled inflammatory immune response or a bacterial or viral infection. It will also be appreciated that certain of the modified particles of present invention can exist in free form for treatment, or where appropriate, as a pharmaceutically acceptable derivative thereof.

The pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The modified particles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

The present invention encompasses pharmaceutically acceptable topical formulations of the inventive modified particles. The term "pharmaceutically acceptable topical formulation", as used herein, means any formulation which is pharmaceutically acceptable for intradermal administration of modified microparticles of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfate, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least the modified particles of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The modified particles can be administered by aerosol. This is accomplished by preparing an aqueous aerosol, liposomal preparation or solid particles containing the modified particles. A nonaqueous (e.g., fluorocarbon propellant) suspension could be used.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It will also be appreciated that the modified particles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

In certain embodiments, the pharmaceutical compositions containing the modified particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

The invention provides methods of regulating an immune response in an individual, preferably a mammal, more preferably a human, comprising administering to the individual the modified particles described herein. Methods of immunoregulation provided by the invention include those that suppress and/or inhibit an innate immune response or an adaptive immune response, including, but not limited to, an immune response stimulated by immunostimulatory polypeptides or viral or bacterial components.

The modified particles are administered in an amount sufficient to regulate an immune response. As described herein, regulation of an immune response may be humoral and/or cellular, and is measured using standard techniques in the art and as described herein.

In certain embodiments, the individual suffers from a disorder associated with unwanted immune activation, such as allergic disease or condition, allergy and asthma. An individual having an allergic disease or asthma is an individual with a recognizable symptom of an existing allergic disease or asthma.

In certain embodiments, the individual suffers from a disorder associated with unwanted immune activation, such as atherosclerosis, ischemic reperfusion injury, and myocardial infarction.

In certain embodiments, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, parancoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

Animal models for the study of autoimmune disease are known in the art. For example, animal models which appear most similar to human autoimmune disease include animal strains which spontaneously develop a high incidence of the particular disease. Examples of such models include, but are not limited to, the nonobeses diabetic (NOD) mouse, which develops a disease similar to type 1 diabetes, and lupus-like disease prone animals, such as New Zealand hybrid, MRL-Fas$^{lpr}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-1 receptor antagonist knockout for rheumatoid arthritis.

In certain embodiments, the individual suffers from a bacterial or viral infection. An individual having a bacterial or viral infection is an individual with a recognizable symptom of an existing bacterial or viral infection.

A non-limiting list of viral infections treatable with the modified particles of the current invention includes herpes virus infections, hepatitis virus infections, west nile virus infections, flavivrus infections, influenza virus infections, rhinovirus infections, papillomavirus infections, paromyxovirus infections, parainfluenza virus infections, and retrovirus infections. Preferred viruses are those viruses that infect the central nervous system of the subject. Most preferred viruses are those that cause encephalitis or meningitis.

A non-limiting list of bacterial infections treatable with the modified particles of the current invention include staphlococcus infections, streptococcus infections, mycobacterial infections, bacillus infections, Salmonella infections, Vibrio infections, spirochete infections, and Neisseria infections. Preferred are bacteria that infect the central nervous system of the subject. Most preferred are bacteria that cause encephalitis or meningitis.

In some embodiments, the invention relates to uses of compositions of this invention prior to the onset of disease. In other embodiments, the invention relates to uses of the compositions of this invention to inhibit ongoing disease. In some embodiments, the invention relates to ameliorating disease in a subject. By ameliorating disease in a subject is meant to include treating, preventing or suppressing the disease in the subject.

In some embodiments, the invention relates to preventing the relapse of disease. For example, an unwanted immune response can occur at one region of a peptide (such as an antigenic determinant). Relapse of a disease associated with an unwanted immune response can occur by having an immune response attack at a different region of the peptide. Since the carboxylated particles of the current invention are free from attached peptides or antigenic moieties, the particles will be effective against multiple epitopes. T-cell responses in some immune response disorders, including MS and other TH1/17-mediated autoimmune diseases, can be dynamic and evolve during the course of relapsing-remitting and/or chronic-progressive disease. The dynamic nature of the T-cell repertoire has implications for treatment of certain diseases, since the target may change as the disease progresses. Previously, pre-existing knowledge of the pattern of responses was necessary to predict the progression of disease. The present invention provides compositions that can prevent the effect of dynamic changing disease, a function of "epitope spreading." A known model for relapse is an immune reaction to proteolipid protein (PLP) as a model for multiple sclerosis (MS). Initial immune response can occur by a response to $PLP_{139-451}$. Subsequent disease onset can occur by a relapse immune response to PLP151-171.

Certain embodiments of this invention relate to treatment of pathological conditions relating to an unwanted hypersensitivity. The hypersensitivity can be any one of types I, II, III, and IV. Immediate (type I) hypersensitivity. The frequency of administration will typically correspond with the timing of allergen exposure. Suitable animal models are known in the art (for example, Gundel et al., Am. Rev. Respir. Dis. 146:369, 1992, Wada et al., J. Med. Chem. 39, 2055, 1996; and WO 96/35418).

Other embodiments of this invention relate to transplantation. This refers to the transfer of a tissue sample or graft from a donor individual to a recipient individual, and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype, and correlating the various possible contributing factors according to well accepted clinical procedures. The immunological assault may be the result of a preexisting immunological response (such as preformed antibody), or one that is initiated about the time of transplantation (such as the generation of TH cells). Antibody, T helper (TH) cells, or cytotoxic T (Tc) cells may be involved in any combination with each other and with various effector molecules and cells. However, the antigens which are involved in the immune response are generally not known, therefore posing difficulties in designing antigen-specific therapies or inducing antigen-specific tolerance. The modified particles of the current invention are particularly useful in preventing the rejection of organs because no attached peptides or antigens need to be conjugated to the modified particles in order for the particles to be effective in inducing tolerance or ameliorate an inflammatory immune response.

Certain embodiments of the invention relate to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but can be resumed if there is any evidence of rejection or inflammation of the graft. Of course, the tolerization procedures of this invention may be combined with other forms of immunosuppression to achieve an even lower level of risk.

EXAMPLES

The following examples are provided to further illustrate the advantages and features of the invention, but are not intended to limit the scope of this disclosure.

Materials and Methods

Virus Propagation

As previously described (Getts et al., J Neurochem. 103:1019, 2007), West Nile Virus (Sarafend strain) was derived from the brains of neonatal mice and used to infect confluent vero cell monolayers, at a multiplicity of infection of 5 plaque forming units (PFU) per cell. Cells were incubated with virus for 40 hours at 37° C., after which they were frozen. Flasks were then thawed and the virus-rich supernatant clarified by centrifugation, after which aliquots were stored at −70° C. until use.

Mice and Infection

Eight to twelve-week old female C57BL/6 (CD45.2) and congenic B6.SJL-PtprcaPep3$^b$/BoyJ (CD45.1) mice were obtained from the Animal Resources Center, Western Australia. C57BL/6-7.2fms-EGFP transgenic (CD45.2) mice were obtained from the Transgenic Animal Resources Center Queensland, Australia. All procedures were performed with permission of the University of Sydney Animal Ethics Committee. All animals were housed under class II biohazard conditions in hepa-filter top cages. Food and water was provided ad libitum.

High dose intra-nasal infection was conducted as previously described with $6 \times 10^4$ PFU WNV in sterile phosphate-buffered saline (PBS; Gibco BRL, Calif., USA). For the low dose infection, mice were inoculated with $6 \times 10^3$ PFU WNV. Mock infection was conducted by inoculating mice with sterile PBS only. (Getts et al., J Neurochem. 103: 1019, 2007, Wacher et al., J Virol. 81: 860, 2007).

Mice were weighed twice daily following infection. Mice were sacrificed under anaesthesia by cardiac perfusion using 40 ml of ice cold PBS. For histology, mice were further perfused with 20 ml of 4% paraformaldehyde (Sigma Aldrich, St Louis, USA) in PBS.

Plaque Assay to Determine Viral Titre

To determine titres of live virus in tissue samples, a plaque assay using virus-susceptible BHK cells (kindly donated by Guna Kapuriah, John Curtin Medical School, Canberra, Australia) was employed. As previously described (Getts et al., J Neurochem. 103: 1019, 2007), tissue samples were dissected from animals and disassociated with a power homogeniser (Tissue Tearor, Biospec, Bartles, Okla., USA). Briefly, five-fold dilutions of clarified homogenates were prepared in Roswell Park Memorial Institute 1640 media (RPMI; CSL Biosciences), and used to infect confluent BHK cells in 6-well plates ($1 \times 10^6$ cells seeded overnight in 2 mL RPMI).

Cells were incubated for 1 hour at 37° C., after which the inoculums were removed by aspiration. Wells were overlaid with 3 ml of 1.5% (w/v) low-gelling Agarose II (Amresco, Solon, Ohio, USA) in 2× Minimum Essential Medium (MEM; GibcoBRL, Grand Island, N.Y., USA). Cells were incubated for a further 3 days at 37° C., after which they were fixed with 3 ml of 10% formalin (Co.) for 2 hr prior to agarose plug removal. A 3% crystal violet (Hopkins and Williams, Essex, England) dye solution in 20% methanol (Fronine, Riverstone, NSW, Australia) was used to stain fixed cells. Plaques were counted using a colony counter (IUL S. A., Barcelona, Spain), and the final PFU per gram (tissue) was determined by factoring the number of plaques, the inoculum volume and sample dilution.

Generation of Chimeric Mice

As previously described (Getts et al., J Neurochem. 103: 1019, 2007), six- to eight-week old B6.SJL-PtprcaPep3$^b$/BoyJ (CD45.1) mice were irradiated with one dose of 950 rads. Twelve hours later, mice were reconstituted with $10^7$ bone marrow cells from C57BL/6-7.2fms-EGFP donors. Mice were given sulfamethoxazole (Sigma Aldrich) and trimethoprim (Sigma Aldrich) in the drinking water for 10 days following irradiation. Mice were infected with WNV six weeks after irradiation, as described above. Chimerism was checked using flow cytometry and was invariably found to be 96-99% of donor origin as previously demonstrated (Getts et al., J Neurochem. 103: 1019, 2007).

Intravenous injection of beads 0.5, 0.05, and 3 μm FITC or Bright Blue (BB) Flouresbrite naked and carboxylated polystyrene beads were obtained from Polyscience, NY, USA. Poly(lactic-co-glycolic acid) (PLGA) naked and carboxylate beads were obtained from Phosphorex, Mass., USA.

Beads were diluted in sterile PBS, and 300 μl was intravenously injected into the tail veins of infected or mock-infected mice. For high dose survival studies ($6 \times 10^4$ PFU WNV i.n.), mice were given one dose of beads each day beginning on day 6 post infection If required, mice were given further injections each day until weight had restabilized. For low dose survival studies ($6 \times 10^3$ PFU WNV i.n.), mice were either injected with beads from d6 p.i., or when significant weight loss was recorded (4-6% of total body weight). Mice were injected with 300 ul of beads once a day for 5 days, or until weight had restabilized. For tissue collection, $6 \times 10^4$ or $6 \times 10^3$-infected mice were injected with 300 μl of beads on either d6 p.i., or when significant weight loss was recorded, and culled when required. Organs were harvested for immunohistochemistry, flow cytometry, plaque assay, and cytokine analysis, as described below.

Immunohistology

Flouresence immunohistochemistry (IHC) was conducted on brain, spleen, liver, lungs and kidneys collected from C57BL/6 and cFMS-EGFP (into B6.SJL-PtprcaPep3$^b$/BoyJ) chimeras. Following perfusion, organs were fixed in 4% paraformaldehyde at 4° C. for 4 hours and then immersed in 30% sucrose overnight, before being frozen in Optimum Cutting Temperature Compound (OCT; Tissue-Tek, Tokyo Japan). Eight-micron tissue sections were cut on a cryostat microtome and air-dried. Fluorescence IHC was performed as previously described, (Getts et al, J Exp Med. 29: 2319, 2007), with the addition of a tyramide-based amplification system (TSA kit; Perkin Elmer, Belgium), used according to the manufacturer's instructions. Tissue sections were counter-stained with DAPI-anti fade (Vector) prior to visualisation.

Microscope and Image Acquisition

Images were acquired on an Olympus BX-51 microscope (Olympus, Japan), using a DP-70 camera and DP manager 2.2.1 software (Olympus).

Isolation of Leukocytes from the Brain and Liver

As previously described (Getts et al, J Exp Med. 29: 2319, 2007) leukocytes were obtained from the brains of PBS-perfused mice by digesting brains for 60 minutes at 37° C. in PBS with deoxy-ribonuclease (0.005 g/ml; Sigma Aldrich) and collagenase IV (0.05 g/ml; Sigma Aldrich). Digestion was stopped with 10% FCS, and the homogenate was passed through a 70 μm nylon cell strainer (Becton Dickinson, N.J., USA). The pellet, obtained after 10 minutes centrifugation at 340×g, was resuspended in 30% Percoll (Amersham, Norway) and layered over 80% Percoll. Leukocytes were collected from the 30%/80% interface after centrifugation at 1140×g for 25 minutes at room temperature. The same protocol is also used to derive leukocytes from the liver, with the tissue weighed before processing.

Isolation of Leukocytes from the Spleen, Blood and Bone Marrow

For flow cytometric analysis, the right femur was dissected out and bone marrow cells flushed out using PBS loaded syringes. For bone marrow precursor isolation, femurs and tibias from at least 4 mice were utilized. The cellular suspension achieved after flushing was filtered through a 70 µm cell strainer and centrifuged for 5 mins at 340 g. Red blood cells in the resulting pellet were lysed in $NH_4Cl$-based red cell lysis buffer (BD Pharm Lyse™; BD Pharmingen), before centrifugation for 5 mins at 340×g. In the case of peripheral blood, blood was collected via cardiac puncture and immediately transferred into citrate buffer (mMol, Sigma Alrich). The resulting suspension was layered over 70% Percoll and centrifuged at 1140×g for 20 minutes at room temperature with the brake off. The interface was collected and the cells washed once in PBS, centrifuged at 340×g. For the isolation of splenic leukocytes, spleens were passed through a 7070 µm cell strainer and centrifuged for 5 mins at 340 g. Red blood cells in the resulting pellet were lysed in $NH_4Cl$-based red cell lysis buffer (BD Pharm Lyse™; BD Pharmingen), before centrifugation for 5 mins at 340×g.

Flow Cytometry

Cells collected (as described above) from the brain, liver, blood, and bone marrow were washed in PBS, and blocked with anti-CD16/CD32 antibody (Biolegend). Viable cells were counted using trypan blue exclusion, which routinely showed >95% cell viability.

Cell surface molecule expression was measured and cell sorts carried out on a FACS ARIA (Becton Dickinson), equipped with an Argon ion and HeNe laser. Viable populations were gated by forward and side scatter and identified fluorescent populations determined by forward-gating thereafter. Sorting was carried out using specific fluorescent and scatter parameters identifying the population of interest. Sorting stringencies was set to purity to achieve >98% purity for bone marrow populations.

Acquired FACS data files were analysed using the flow cytometry program, Flow Jo (FlowJo, Ashland, Oreg., USA). Quantification of cell populations of interest were calculated based on flow cytometry percentages at analysis and absolute cell counts from each organ.

Adoptive Transfer

Both $Ly6C^{hi}$/cFMS-EGFP$^+$/CD11b$^+$ and $Ly6C^{lo}$/Cfms-EGFP$^+$/CD11b$^+$ populations were sorted from day 6 intranasally WNV-infected mice. $Ly6C^{hi}$ BM was labeled with 10 mM cell tracker orange (CMTMR [5-(and -6)-(((4-chloromethyl) benzoyl) amino) tetramethylrhodamine)-mixed isomers; Invitrogen). Sorted cells were centrifuged and raised in 1 ml PBS containing 10 µM CMTMR. Cells were stained for 10 min before the reaction was stopped with 10% FCS. Cells were washed in 50 ml PBS at least three times. Labeled CMTMR $Ly6C^{hi}$ BM cells were then mixed 1:1 with $Ly6C^{lo}$ cells, which, except for the addition of CMTMR, had been treated similarly to $Ly6C^{hi}$ populations. A total of 2×10$^6$ BM cells were i.v. injected into either day 6.5 WNV-infected or mock-infected Ly5.1-057BL/6 congenic mice. This was immediately followed by an intravenous injection of 300 ul BB polystyrene beads. 12 h later, brains, spleens and livers were harvested as described above. The presence of donor cells was investigated using flow cytometry, both using cFMS-EGFP and CMTMR-cell tracker orange.

Multiplex ELISA

Multiplexed plate ELISAs were performed according to the manufacturers instructions (Quansys Biosciences, Logan, Utah, USA). Briefly, brain, spleen, and liver tissue were homogenized in PBS, clarified by a 1000×g spin, and stored at −20° C. until the assay was performed. Serum samples were also used. Thawed samples and standards were diluted in the provided buffer, and 30 µl of each were plated in each well that contains 16 spots each containing a capture antibody for a particular soluble protein. Plates were then incubated for 1 hour on an orbital shaker at 120 r.p.m. Plates were washed 3 times, and 30 µl of detection antibody was added to each well and incubated for another hour. After washing 3 times, strepavidin-HRP was added and incubated for a further 15 minutes. Plates were then washed 6 times, and substrate mix was added. Plates were immediately read on a CCD imager (Kodak, Rochester N.Y., USA). Plate images were analysed using Quansys Q-view software (Quansys Biosciences).

Induction and Evaluation of Experimental Autoimmune Encephalitis (EAE)

C57BL/6 mice were injected sub-cutaneously with emulsion containing 0.1 mg MOG Peptide (MEVGWYR-SPFSRVVHLYRNGK; Auspep, Parkville, Victoria, Australia; >95% HPLC purified) and Complete Freund's adjuvant containing 2 mg/mL Mycobacterium tuberculosis (Sigma Aldrich). Two days later, mice were administered 500 µl Pertussis toxin (Sigma Aldrich) i.p. Mice were monitored for disease progression, and graded on the following scale: 1, limp tail and/or weakness of 1 hind limb; 2, weakness in more than one limb, gait disturbance; 3, paralysis in 1 limb; 4, paralysis in more than one limb, incontinence; 5, moribund.

Induction of Thioglycolate-Induced Peritontitis

The induction of peritonitis was performed by the injection of 1 ml thioglycolate (4% (w/v); Sigma Alrich) dissolved in PBS. Intraperitoneal lavage was performed on mice sacrificed by cervical dislocation. Briefly, 5 ml of peritoneal lavage buffer (PLB; PBS containing 0.5 mM EDTA (Fronine) with heparin (Sigma Aldrich) 9.9 units/ml) was injected into the peritoneum. The peritoneum was gently massaged before the PLB was aspirated into a 10 ml syringe. This process was repeated twice. The lavage was then raised to 50 ml in PLB and spun at 340×g for 5 minutes. Cells were prepared for flow cytometry as described above.

Statistics

Graphs were made and computerized statistical analysis was performed in GraphPad Prism, and InStat, respectively (both programs from GraphPad software, San Diego, Calif., USA). Depending on the data, an unpaired, two-tailed Student t-test, or one way ANOVA with a Tukey-Kramer post test was performed, with P<0.05 considered to be significant. For correlation analysis between parameters such as weight loss, infiltration, and virus titre, a non-linear regression (curve fit) was used, with a second order polynomial $(Y=A+B*X+C*X^2)$.

Example 1

Characterization of the High and Low Does Models of WNV Encephalitis

Figure 1:
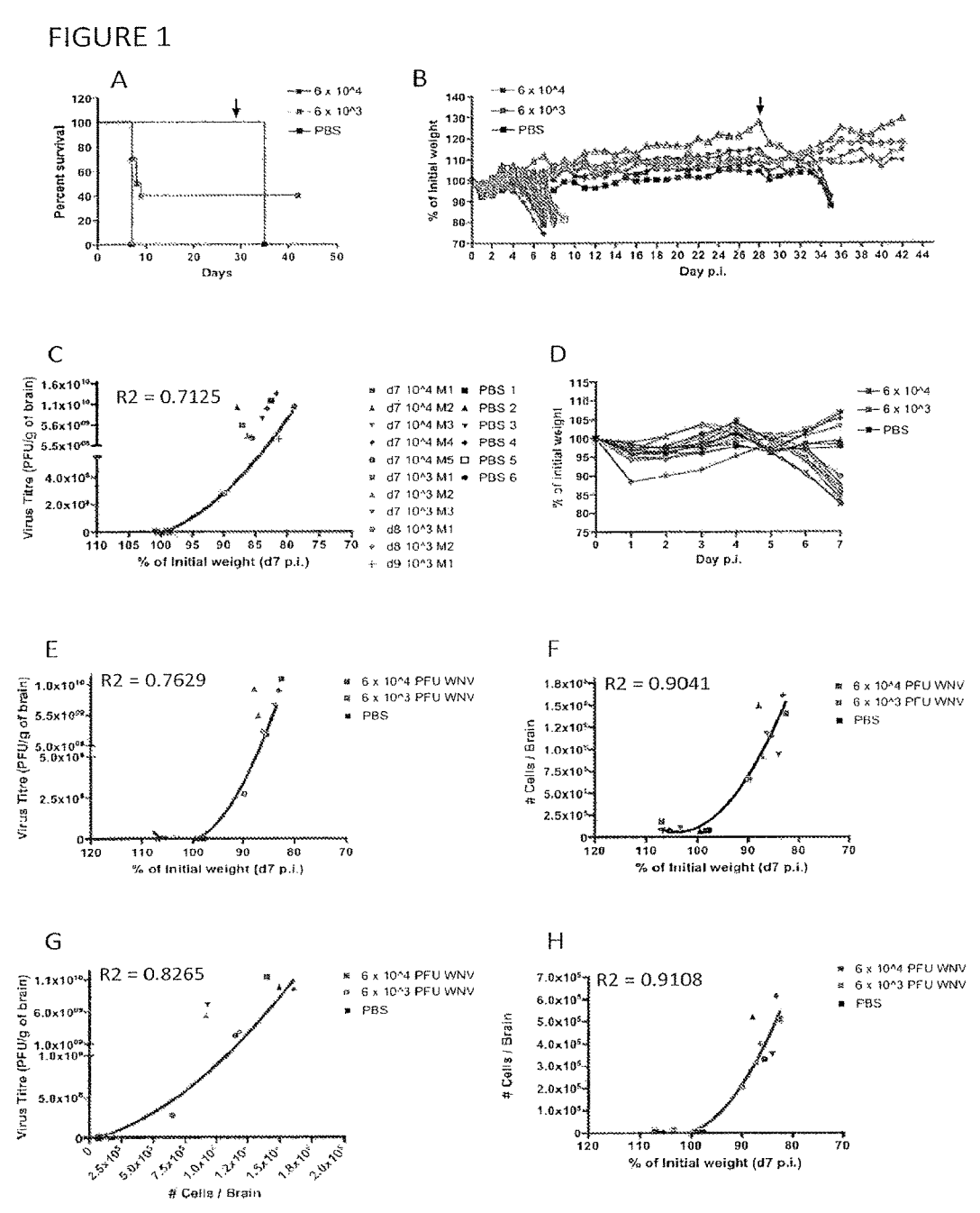

High dose infection of C57BL/6 mice with 6×10$^4$ PFU WNV i.n. results in 100% mortality on d7 p.i. (FIG. 1A). Macrophages and immigrant microglia, which we have previously shown to derive from circulating $Ly6c^{hi}$ monocyte precursors (Getts et al, J Exp Med. 29: 2319, 2007), infiltrate the WNV-infected brain from d5 p.i. T cells, NK cells, and neutrophils also enter the CNS from this timepoint onwards, with the peak of infiltration seen on d7 p.i. (FIG. 1F-H, FIG. 2A-D) Brain virus titre also exponentially increases from d5 p.i., reaching high levels on d7 p.i. (FIG. 1C), and body weight of infected mice significantly decreases from d5 p.i. until death (FIG. 1B).

Inoculation of mice with 10-fold less virus, i.e. $6\times10^3$ PFU i.n., produces sub-lethal outcomes. Some variability occurs in mortality rate when comparing independent experiments, which ranges between 40-60% (FIG. 1A); however, a strong correlation between the percentage of weight loss and virus titre/infiltration has been consistently shown (FIG. 1B-H, FIG. 2A-E). The daily monitoring of mouse weight has proven to be a reliable method to predict the outcome of infection in individuals, and is indicative of when mice require intervention in order to survive infection (FIG. 1B).

Mice that do not lose weight after inoculation with $6\times10^3$ WNV do not succumb to infection, and are immune to subsequent reinfection with $6\times10^4$ (FIG. 1A-B). These mice do not show any symptoms of illness upon initial infection or high dose reinfection, including weight loss. Conversely, mice that lose a significant amount of weight compared to the normal fluctuations of mock-infected controls (usually >4% of body weight in a 24 hour time period) continue to lose weight, typically for 2-3 days before death occurs. In this model of encephalitis, the majority of mice that succumb to infection begin to lose weight between d6 and d11 post infection, and death occurs before d16 p.i. These mice show high titres of virus in the brain at TOD, comparable to d7 mice infected with $6\times10^4$ (FIG. 1C).

Flow cytometry comparing leukocyte infiltration in the brains of $6\times10^4$ and $6\times10^3$-infected mice has revealed that percentage weight loss on d7 p.i. strongly correlates with the infiltration of total leukocytes (FIG. 1F), macrophages (FIG. 1H), immigrant microglia (FIG. 2A), T cells (FIG. 2C), and NK cells (FIG. 2E), with some correlation shown between weight loss and neutrophil immigration (2D). Not surprisingly, numbers of $CD45^{lo}$ microglia remained relatively unchanged in all mice, as this population mainly comprises the resident microglia of the brain (FIG. 2B).

To further investigate the low dose model of infection, $6\times10^3$-infected mice were weighed daily and sacrificed on d0-d14, with brains harvested for flow cytometry and plaque assay. Some correlation was shown between percentage weight loss at time of sacrifice and virus titre (FIG. 2F), or leukocyte infiltration (FIG. 2G). However, a comparison between virus titre and leukocyte infiltration revealed that some mice had high titres of virus without significant infiltration (FIG. 2H), and while some of these mice had also lost a significant amount of weight, others had not (FIG. 2F). Because mice have to be sacraficed to determine virus titres in the brain, it is unclear whether these mice that had virus in the brain without significant weight loss or leukocyte infiltration would clear the virus without showing weight loss or infiltration, or if the high virus titre seen precedes infiltration of the brain/weight loss.

Example 2

Carboxylated Bead Treatment Significantly Improves Survival in the High and Low Dose Models of WNV Encephalitis Fluorescent beads have been used frequently in the literature to follow the trafficking of monocyte subsets in various in vivo models of disease. However, these studies overlook the potential influence that these theoretically "inert" beads may have on monocyte function, and as a result, the outcome of disease.

In an attempt to track monocytes during WNV infection, we used both naked, and carboxylated polystyrene beads, and found an unexpected alteration on the course of disease. The following data reveal that both naked and carboxylated polystyrene beads significantly reduce infiltration of the brain by immune cells, and promote long-term survival of infected mice.

Figure 3:
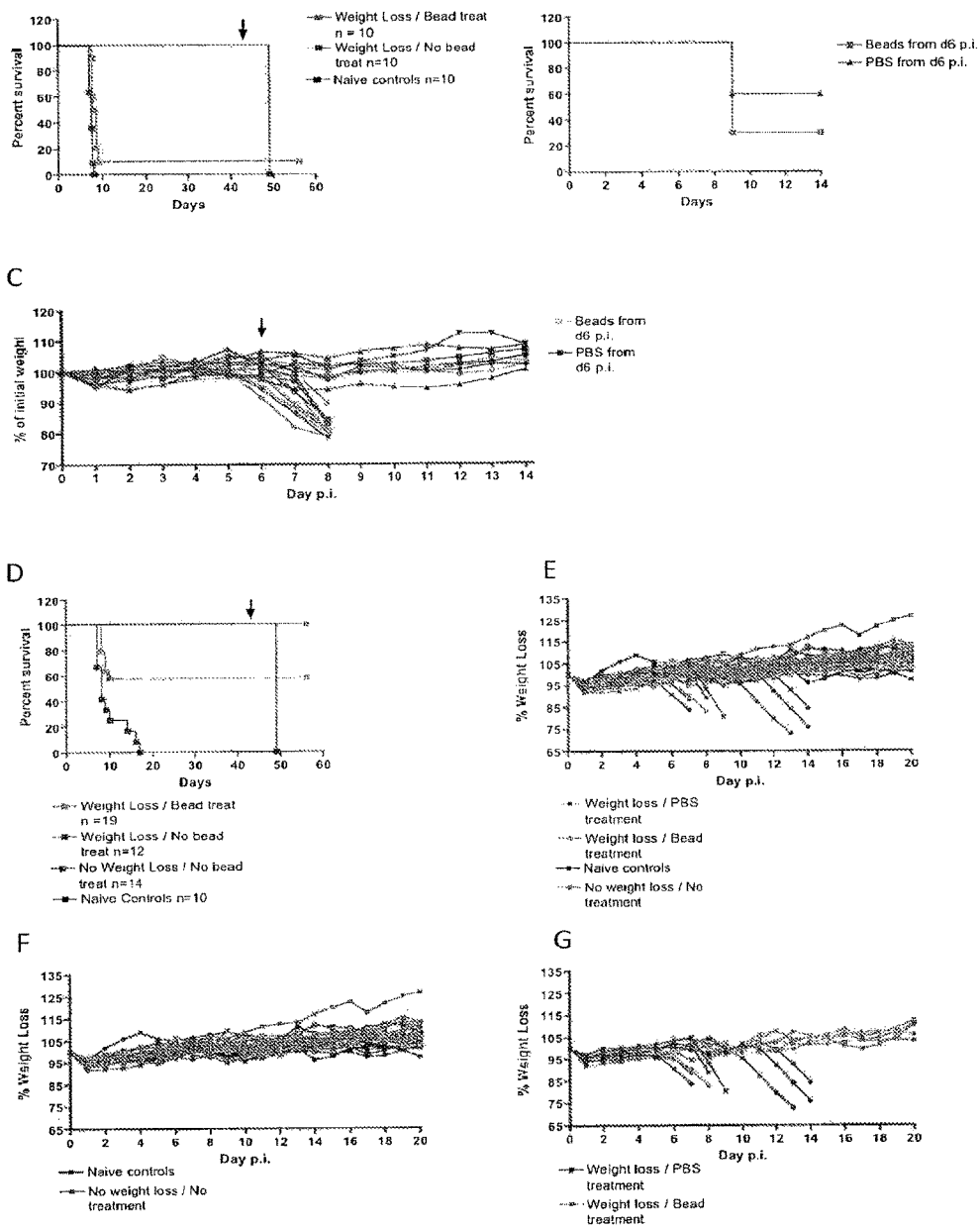
FIG. 3 (A) shows the long term survival of mice treated with carboxylated polystyrene beads in PBS at day 6 after infection with high dose WNV; (B) shows that treating low dose WNV-infected mice with carboxylated polystyrene beads beginning at day 6 post infection is ineffective at prolonging survival of mice; (C) shows that treating low dose WNV-infected mice with carboxylated polystyrene beads beginning at day 6 post infection is ineffective at preventing weight loss in mice compared to control mice; (D) shows that treatment of low dose WNV-infected mice is effective at prolonging survival of mice when the beads are administered upon weight loss in the mice. (E-G) shows weight loss recorded in these mice up to 20 days pi.

Injection of $6\times10^4$ WNV-infected mice with $4.41\times10^9$ 0.5 μm carboxylated polystyrene beads in 300 μl PBS on d6 p.i. i.v. resulted in 10% long-term survival of mice in this lethal model of disease (FIG. 3A). To see if survival outcomes could be improved, we also injected this same concentration of beads into mice infected with the lower dose of $6\times10^3$ on d6 p.i. However, this strategy reduced survival of treated mice as compared to PBS-treated controls (FIG. 3B). These results emphasize that beads need to be administered therapeutically i.e. when mice initially show significant weight loss, which we have shown to be indicative of high virus titre and infiltration of the brain by leukocyte populations (see FIG. 1,2).

Therefore we adopted a therapeutic approach to bead administration in the low dose model of infection. Mice were weighed daily (FIG. 3E-G), and $4.41\times10^9$ carboxylated polystyrene beads were administered if significant weight loss was detected in a 24-hour time period (usually >4% of total body weight, as compared to the normal fluctuations of mock-infected controls). Using this strategy, we were able to increase survival of mice that would usually continue to lose weight and die without intervention, by 60% (40-80% in independent experiments) (FIG. 3D). As expected, all mice that lost weight and were treated with PBS continued to lose weight and died 2-4 days later (FIG. 3E, G). Mice that did not lose a significant amount of weight at any time showed similar stability in weight as PBS-infected controls (FIG. 3E-F).

Figure 4:
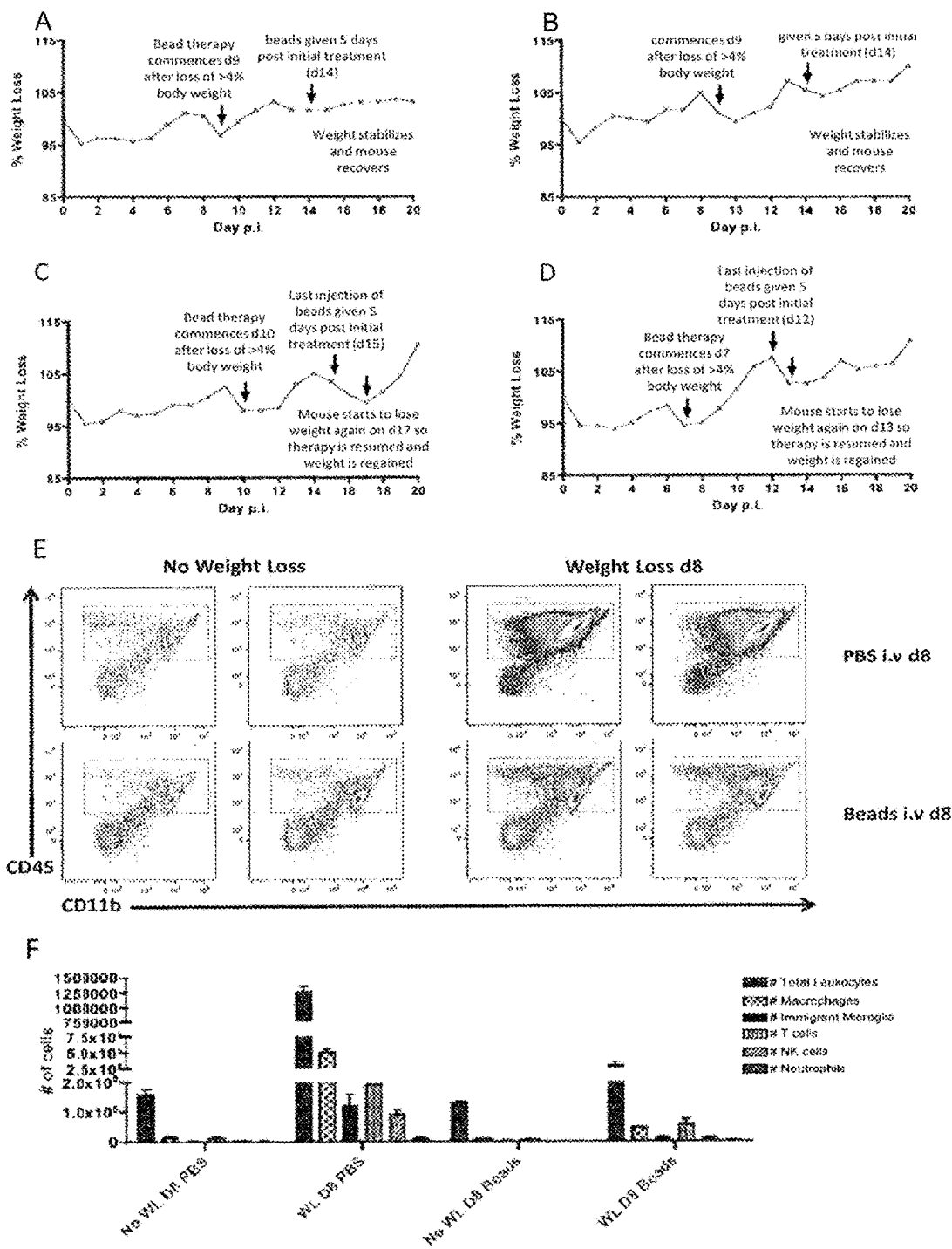
FIG. 4 (A-D) are examples of treating low dose WNV-infected mice with carboxylated polystyrene beads upon weight loss in the mice the mice in (A-B) only require bead treatment for 5 days and weight remains stable and they go on to survive without further bead treatment, whereas the mice in (C-D) begin to lose weight again when bead treatment is ceased after 5 days, so treatment resumes until weight restabalizes (E) shows the infiltration of CD45$^+$ CD11b$^+$ macrophages into the brains of low dose WNV-infected mice at 9 days post infection, that either lost weight or did not lose weight and were treated with either PBS or carboxylated beads at day 8 post infection; (F) is a graphical representation of the types of cells found infiltrating the brain of WNV-infected mice at 9 days post infection, that either lost weight or did not lose weight and were treated with either PBS or carboxylated beads at day 8 post infection.

Mice were treated with carboxylated beads for 5 consecutive days upon the initial detection of significant weight loss. In some mice, 5 days of bead treatment was sufficient and weight remained stabilized after bead injection ceased and these mice went on to survive infection without further intervention (FIG. 4A-B). However, some mice began to lose weight again when bead treatment ceased at 5 days, so treatment was recommenced until weight restabalized, and these mice also survived long-term (FIG. 4C-D).

Flow cytometry was conducted on d9 p.i. on brains of $6\times10^3$ WNV-infected mice that were either treated with carboxylated polystyrene beads or PBS when significant weight loss was detected on d8 p.i. Mice that had not lost weight were also bead- or PBS-treated on d8 as controls for the experiment. As shown in FIGS. 4D-L, mice that did not lose weight on d8 p.i. but were bead-(FIG. 4H-I) or PBS-treated (FIG. 4D-E) showed no infiltration of the brain by monocyte-derived macrophages or immigrant microglia, T cells, NK cells or neutrophils, with the main population isolated being the $CD45^{lo/int}$ $CD11b^+$ resident microglia. In mice that did lose weight on d8 p.i. and were treated with PBS, a massive infiltration of the brain was evident on d9 p.i. (FIG. 4F-G), with the main population being the $CD45^{hi}$ inflammatory monocyte-derived macrophages (FIG. 4L). However, in the mice that lost weight and were treated with beads on d8 p.i., a significant infiltrate was still present, but was greatly reduced in comparison to PBS-treated mice (FIG. 4J-L). Flow cytometry of $10^3$-infected mice treated with bead or PBS upon weight loss needs to be repeated to show that reductions in infiltration occur when mice are bead-treated across days 6-14 p.i.

Example 3

Carboxylation of Beads is Critical for Significant Improvement in Survival and Changes in Leukocyte Populations in WNV-Infected Mice At this stage of investigation, it was unclear whether the carboxylation of beads was critical for the improvements seen in survival and reductions in leukocyte trafficking to the brain. $6 \times 10^3$ WNV-infected mice were injected with $4.41 \times 10^9$ 0.5 µm naked or carboxylated beads in 300 µl PBS i.v., or PBS only, when significant weight loss was recorded. Mice injected with carboxylated beads showed a significant improvement in survival of 60%, whereas naked bead-treated mice showed a much smaller improvement of 25% (FIG. 5A). Mice that did not lose weight were not treated and survived infection without intervention, whereas mice that lost weight and were treated with PBS all died by d14 p.i. (FIG. 5B-D). Weight loss was monitored in these mice up to d20 p.i.; mice that did not lose a significant amount of weight showed a similar pattern of stability as PBS-infected controls (data not shown), whereas mice that were treated with either carboxylated or naked beads (FIG. 5B-C) eventually stabilized and survived, or continued to lose weight and died 2-4 days later. All mice that lost weight and were treated with PBS (B, D) continued to lose weight and died 2-5 days later.

To investigate the changes in leukocyte populations and determine which cells could be found in association with either carboxylated or naked beads, flow cytometry was conducted on mice infected with $6 \times 10^4$ PFU WNV. Mice were injected with $4.41 \times 10^9$ carboxylated FITC-beads or naked FITC-beads, delivered i.v. in 300 ul PBS, or PBS alone, on d6 p.i. Mice were sacraficed on d7 p.i., and blood, brain, bone marrow, liver and spleen was collected for flow cytometry.

"Free" beads, as well as beads in association with $CD45^+$ leukocytes, could be detected by flow cytometry (Ex/Em Max 441/486 nm). As expected, beads could not be detected in the blood of PBS-treated controls (FIG. 5E-G), but could be seen in naked (FIG. 5H-J) and carboxylated (Figure L-M) bead-treated mice. Beads appeared to be cleared more effectively when they were carboxylated, and of those that remained in the circulation, many were in association with CD45+ leukocytes (FIG. 5O), as compared to naked beads (FIG. 5K), which were primarily "free". This data suggests that the carboxylation somehow promotes the uptake of beads from the circulation by leukocytes as compared to naked beads, some of which still remain "free" in the circulation 24 hours post injection.

Flow cytometry of the brain revealed some significant differences in the reduction of leukocyte populations in the brains of mice treated with either carboxylated or naked beads. Carboxylated or naked beads could not be detected in the brain on d7 p.i., 1 day post-treatment (FIG. 6A-C), which suggests that cells taking up the beads did not enter the infected CNS. The total number of leukocytes in the brains of both naked and carboxylated bead-treated mice was significantly reduced as compared to PBS-treated controls, as well as total macrophage and microglial populations (FIG. 6D). However, only carboxylated beads reduced the numbers of T cells and NK cells in the brains of these mice. Both $Ly6c^{hi}$ and $Ly6c^{lo/int}$ populations of macrophages were significantly reduced by both bead treatments, with no changes seen in the small population of $Ly6c^-$ cells. As for $CD45^{int}$ activated microglia, reductions in the $Ly6c^{hi}$ subset were only seen with carboxylated bead treatment, but reductions in $Ly6c^{lo/int}$ and $Ly6c^-$ subsets were seen with both bead treatments. No changes were seen in the small subset of $Ly6c^{hi}$ $CD45^{lo}$ resting microglia, however both bead treatments reduced $Ly6c^{lo/int}$ and $Ly6c^-$ subsets significantly.

Flow cytometry of the spleen revealed that many beads were taken up by leukocytes in this organ, with some interesting differences in populations between treatments. As shown in FIG. 7A-I, bead+ cells were primarily $CD11b^+$, $CD11c^-$ and $Ly6c^+$.

Further analysis showed that three main subsets of interest were found to take up beads in the spleen—the $CD11b^+$, $CD11c^-$ monocytes (FIG. 7J, M, P), the $CD11b^+$, $CD11c^+$ "myeloid" dendritic cells, primarily $Ly6c^{lo/-}$ (FIG. 7K, N, Q), and the $CD11b^-$, $CD11c^+$ dendritic cells, primarily $Ly6c^{lo/-}$ (FIG. 7L, O, R).

Figure 8:
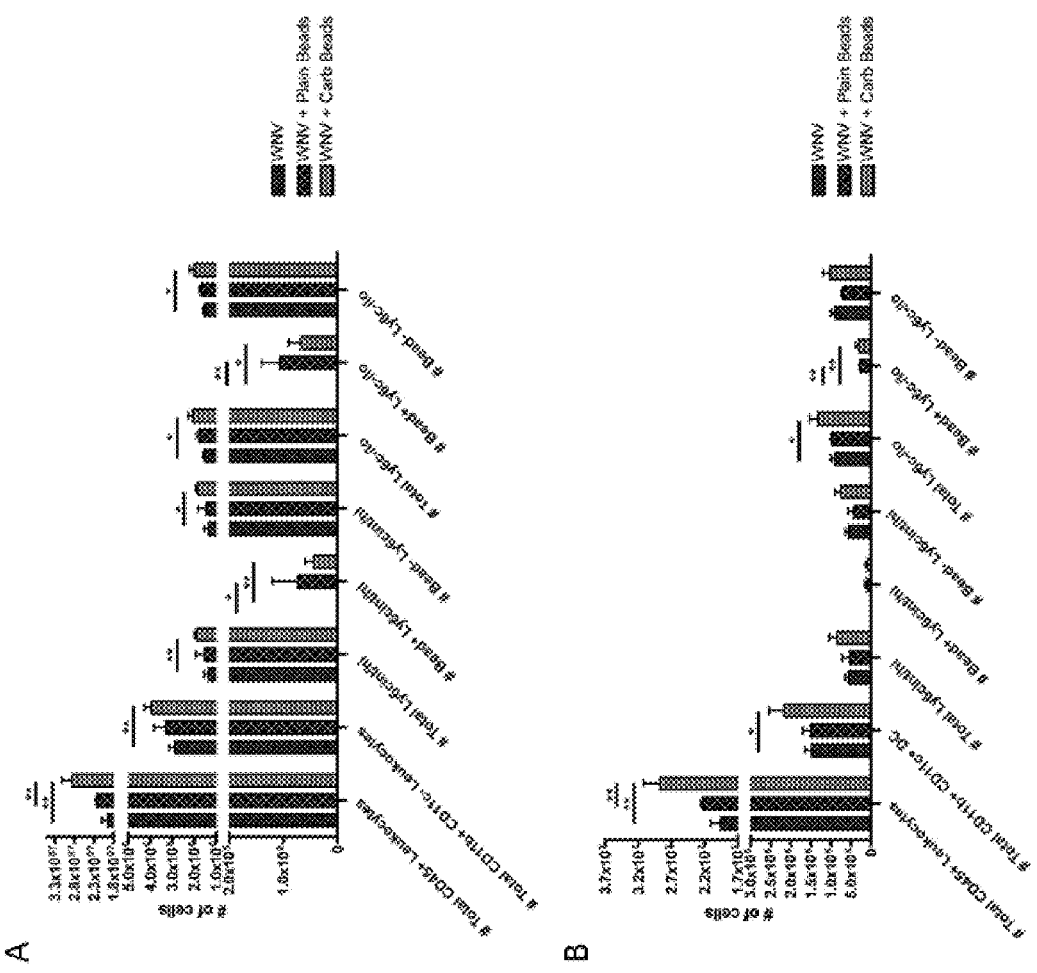
FIG. 8 shows the ability of FITC-conjugated polystyrene carboxylated beads or FITC-conjugated naked polystyrene beads to be taken up by and increase the numbers of CD11b$^+$ CD11c$^-$ monocytes (A) and CD11b$^+$ CD11c$^+$ (B) or CD11b$^-$ CD11c$^+$ (C) dendritic cells in the spleen after infection with high dose WNV.
Figure 9:
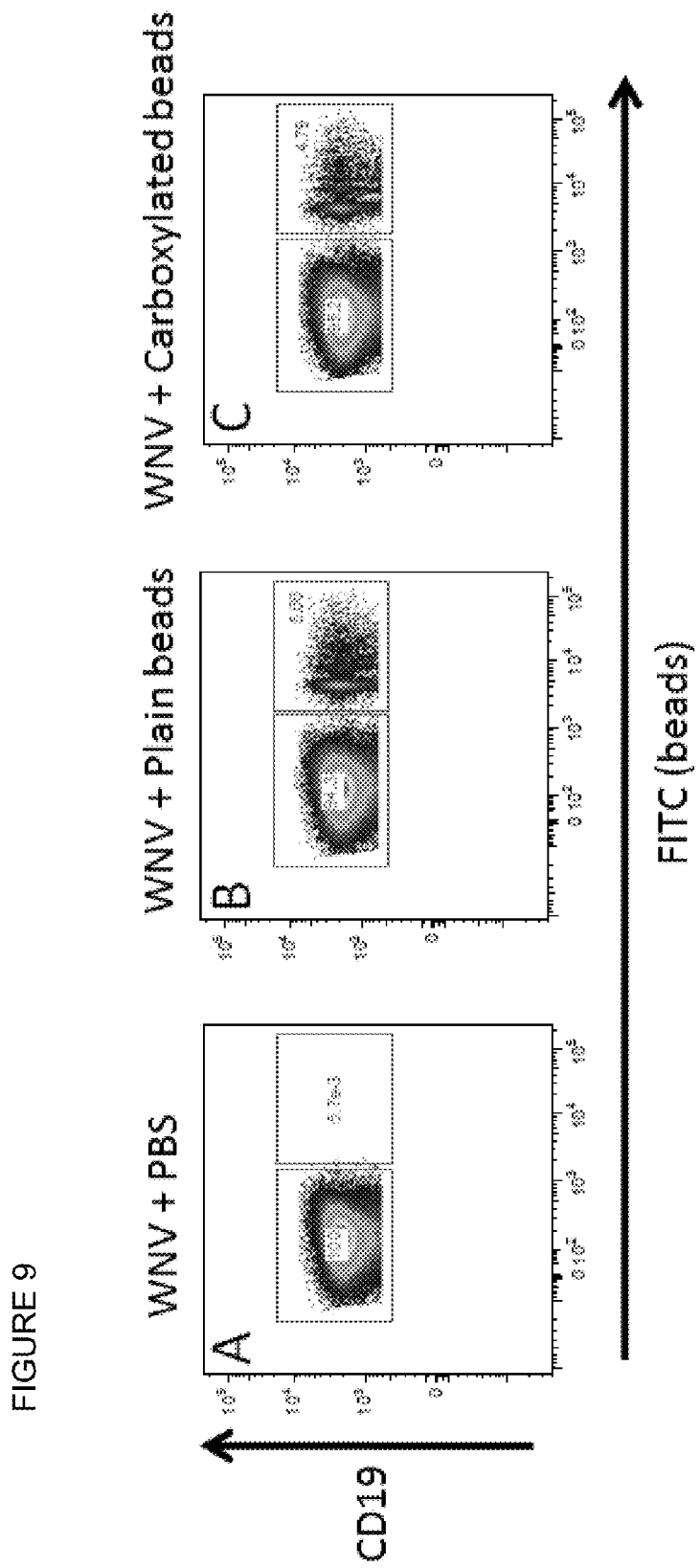
FIG. 9 shows (A-D) the ability of FITC-conjugated carboxylated polystyrene beads or FITC conjugated naked polystyrene beads to be taken up by and increase the numbers of CD19$^+$ B cell and CD3$^+$ T cell subsets in the spleen after infection with high dose WNV.
Figure 9:
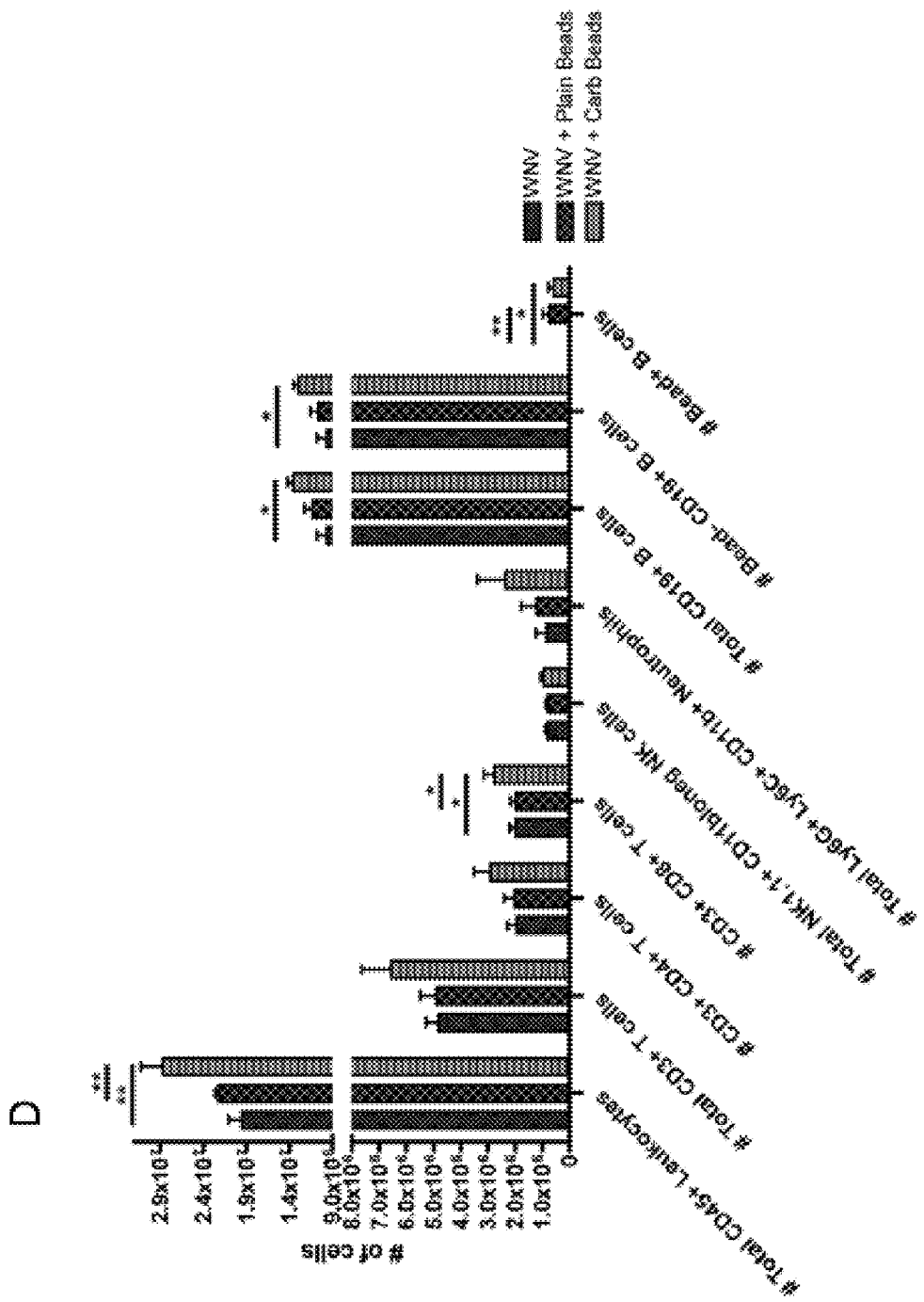
Figure 10:
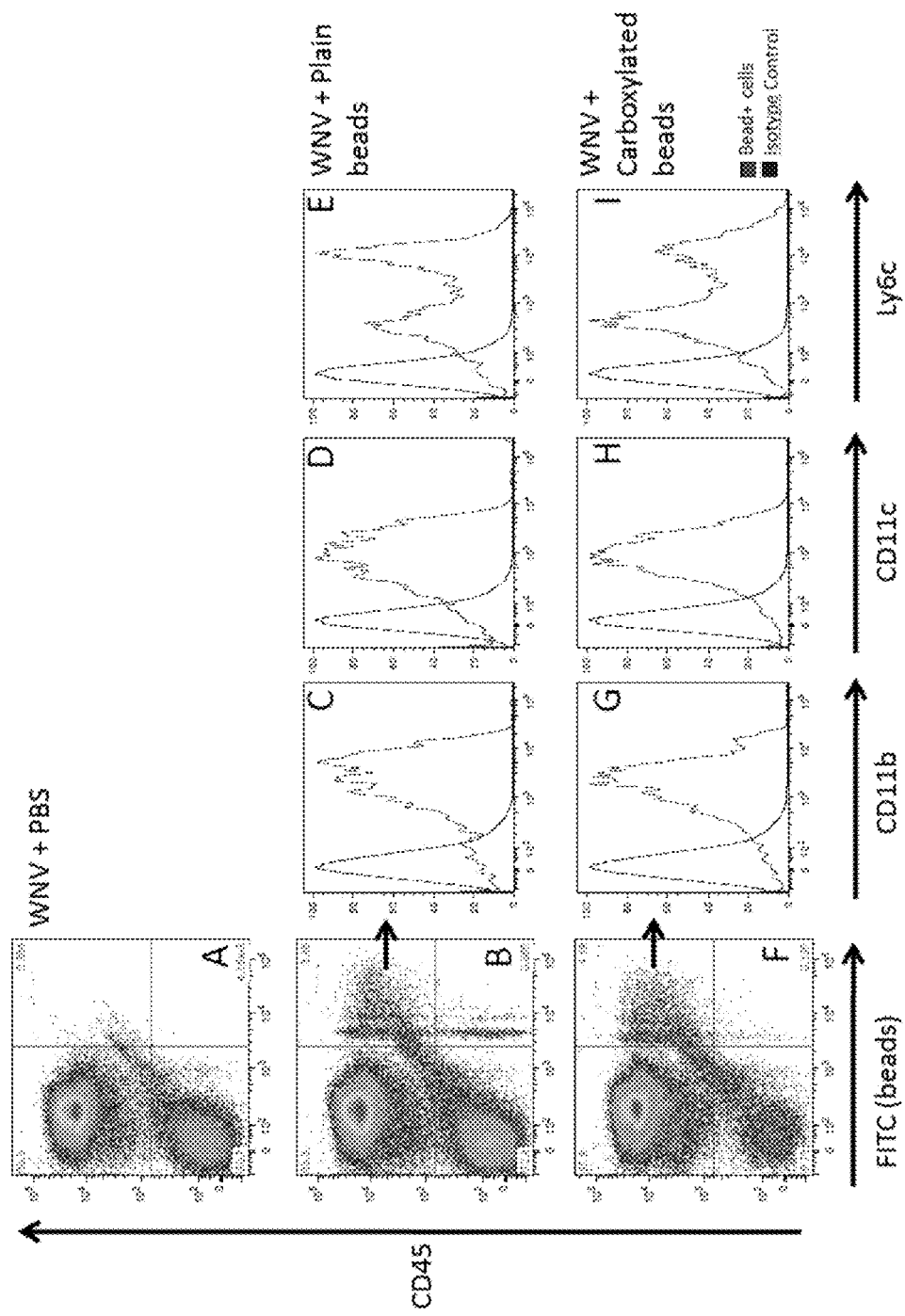
FIG. 10 shows (A-L) the ability of FITC-conjugated carboxylated polystyrene beads or FITC conjugated naked polystyrene beads to be taken up by CD11b$^+$ (C,G), CD11c$^+$ (D,H), and Ly6c$^+$ (E,I) cells, specifically, within CD11b$^+$ CD11c$^-$ monocytes (J) and CD11b$^+$ CD11c$^+$ (K) or CD11b$^-$ CD11c$^+$ (L) dendritic cells, in the liver after infection with high dose WNV.
Figure 11:
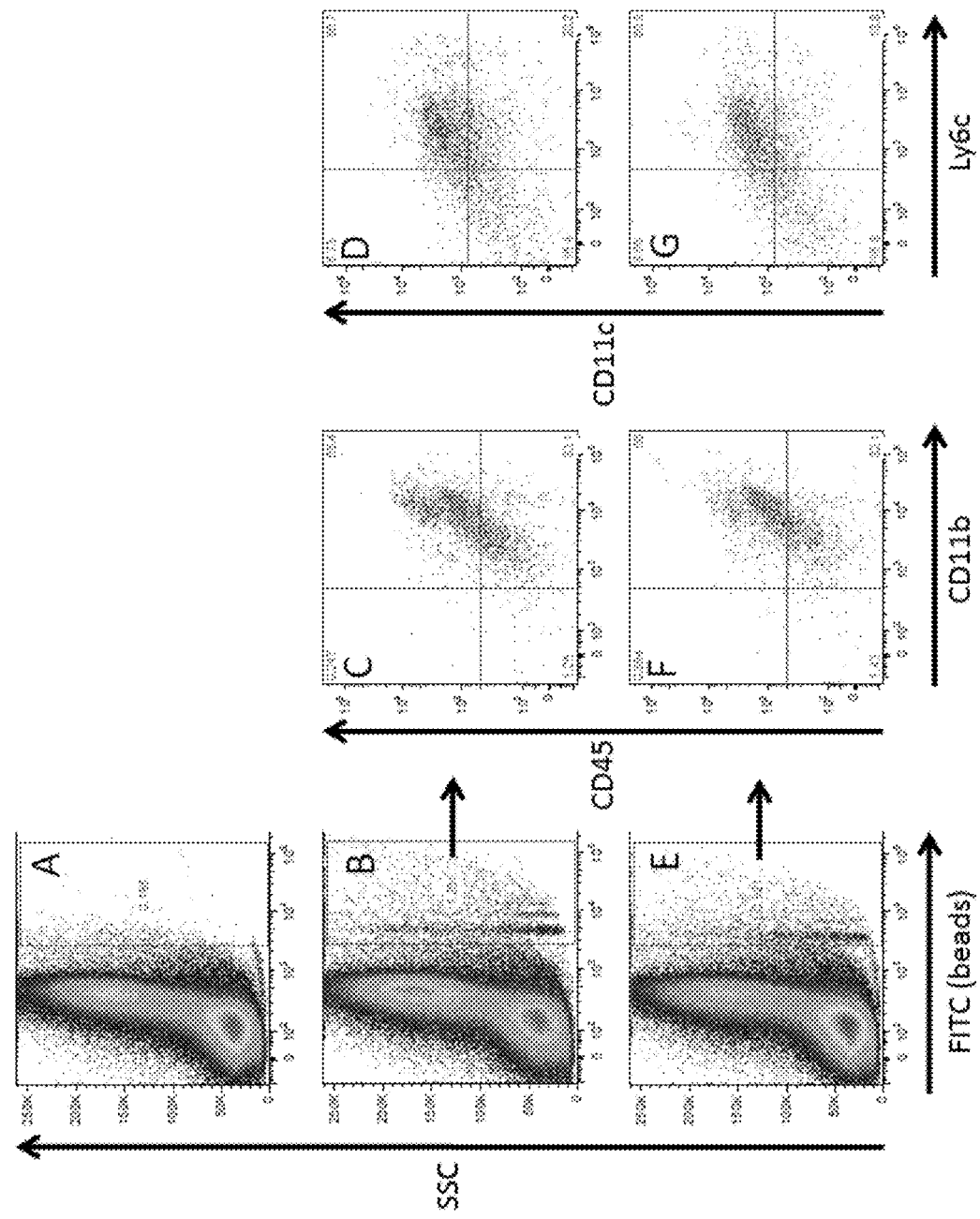
FIG. 11 shows (A-G) the ability of FITC-conjugated carboxylated polystyrene beads or FITC conjugated naked polystyrene beads to be taken up by CD11b$^+$, (C,F), CD11c$^+$ and Ly6C$^+$ (D,G) cells, in the bone marrow after infection with high dose WNV.

Increases in these 3 populations of cells were also apparent in the spleen of carboxylated bead-treated mice. Increases in total $CD11b^+$, $CD11c^-$ monocytes, as well as total $Ly6c^{int/hi}$ bead$^+$ $Ly6c^{int/hi}$, and bead$^-$ $Ly6c^{int/hi}$ subsets were found in carboxylated-treated mice (FIG. 8A). Total $Ly6c^{-/lo}$, bead$^+$ $Ly6c^{-/lo}$ and bead$^-$ $Ly6c^{-/lo}$ were also found to increase with carboxylated bead treatment. These data suggest that monocytes may traffick to the spleen as a result of carboxylated bead treatment, and not only bead$^+$ but also bead$^-$ cells are recruited.

Of the $CD11b^+$ $CD11c^+$ dendritic cells in the spleen, the $Ly6c^{-/lo}$ population was found to take up both types of beads (FIG. 8B). However, only carboxylated beads increased the total numbers of $CD11b^+$ $CD11c^+$ dendritic cells in the spleen, and of these, the $Ly6c^{-/lo}$ population. As there was no increase in bead$^-$ $Ly6c^{-/lo}$ dendritic cells, it is apparent that only bead$^+$ $Ly6c^{-/lo}$ dendritic cells traffic to the spleen after the uptake of carboxylated beads. It is possible that these cells are in fact derived from $Ly6c^{hi}$ inflammatory monocytes that take up beads in the circulation, divert to the spleen instead of trafficking to the brain, where they down regulate Ly6c expression, and upregulate CD11c expression as they differentiate into dendritic cells.

Of the $CD11b^-$ $CD11c^+$ dendritic cell populations in the spleen, $Ly6c^{lo/-}$ cells took up both bead types (FIG. 8C). With carboxylated bead treatment increases were seen in total numbers of $CD11b^-$ $CD11c^+$ dendritic cell populations, more specifically $Ly6c^{lo/-}$ cells. Increases were seen in both bead$^+$ and bead$^-$ cells of this population, suggesting that not only bead$^+$ but also bead$^-$ cells increase in the spleen. This population may comprise of splenic resident DC, non-myeloid DC recruited from the periphery, or may also potentially consist of inflammatory monocytes that have taken up beads, down regulated CD11b and Ly6c and upregulated CD11c expression.

Beads were also found in association with a small percentage of B cells in the spleen, however only carboxylated beads significantly increased the number of B cells in the spleen (FIG. 9A-D). The only other significant increase seen in the spleen was in CD8+ T cells while numbers of CD4+ T cells, NK cells, and neutrophils remained unchanged.

Beads could also be detected in the liver, primarily in association with CD11b, CD11c and Ly6c-expressing cells (FIG. 10A-I). As for the spleen, $CD11b^+$ $CD11c^-$ monocytes (FIG. 10J), $CD11b^+$ $CD11c^+$ (FIG. 10K) and $CD11b^-$ $CD11c^+$ (FIG. 10L) dendritic cells were found to take up beads in the liver. However, there was no significant increases or decreases in any leukocyte populations of the liver. A small number of beads were also detected in the bone marrow, in a small population of $CD11b^+$ $CD11c^+$ $Ly6c^+$ leukocytes (FIG. 11A-G). However, there were no significant increases or decreases found in any leukocyte populations of the bone marrow.

Example 4

Figure 12:
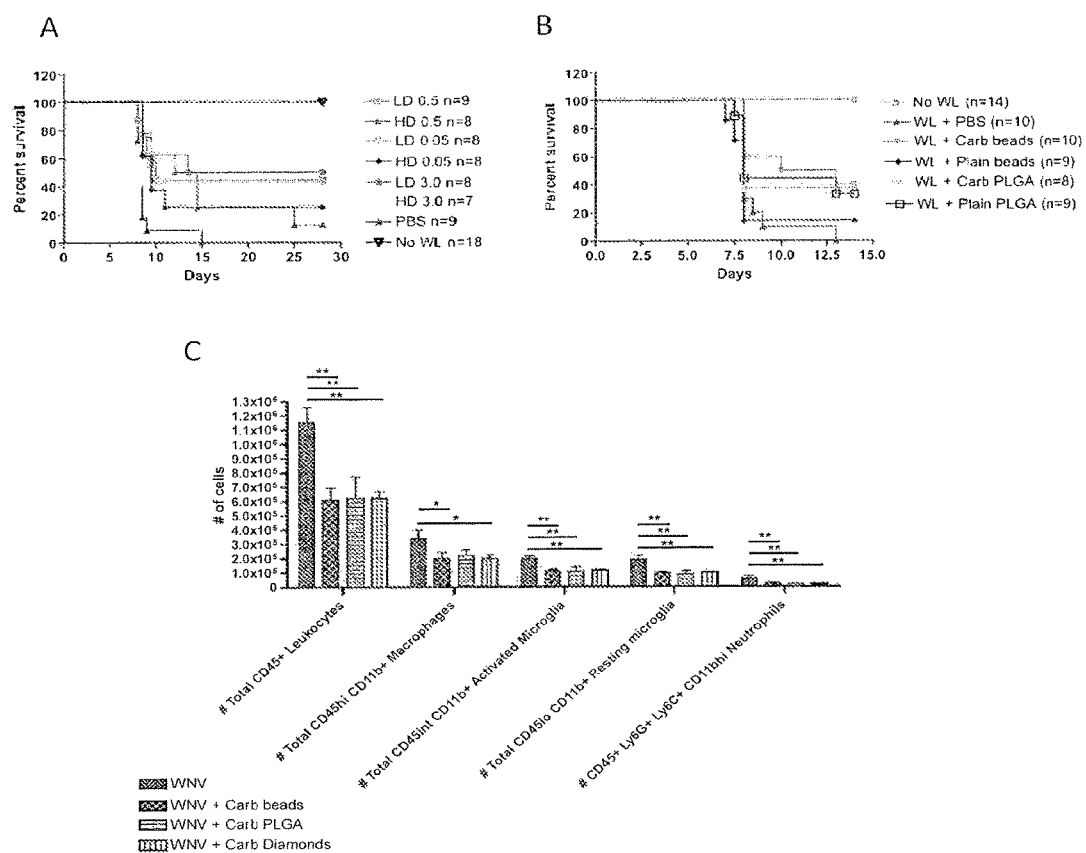
FIG. 12 shows (A) the percent survival of low dose WNV-infected mice treated with high dose or low dose carboxylated polystyrene beads of different sizes; (B) shows the percent survival of low dose WNV-infect mice treated with FITC-conjugated carboxylated beads, naked FITC-conjugated beads, carboxylated PLGA spheres or naked PLGA spheres; (C) shows the infiltration/activation of various monocyte populations in the brain of mice infected with low dose WNV and treated with carboxylated FITC-beads, carboxylated-FITC PLGA spheres, or carboxylated nanodiamonds.

$6 \times 10^3$ WNV-infected mice were injected with a low dose of 0.1% or a high dose of 0.5% beads of 0.5, 0.05, or 3 μm carboxylated polystyrene beads in 300 μl PBS i.v., or PBS only, when significant weight loss was recorded. Mice that were treated with a low dose of 0.5, 0.05, or 3 μm showed similar improvements in survival, of approximately 40-50% (FIG. 12A). However, high dose treatment of mice appeared to be detrimental to survival, with a much smaller improvement of 20%. A significant number of the mice treated with the high dose of beads showed atypical symptoms of illness, and it could be speculated that the build up of such a high dose of beads in the vital organs over a number of days was detrimental to the mouse. This time course will be repeated, with the potential for including other lower doses of beads. Flow cytometry will also be conducted in $6 \times 10^4$ WNV-infected mice treated on d6 p.i. with different sizes of beads.

These data highlight the fact that carboxylated polystyrene beads may not broken down in vivo, and thus may have limited therapeutic applicability. We therefore obtained 0.5 μm biodegradable poly(lactic-co-glycolic acid) (PLGA) spheres that were either carboxylated or naked (however the naked spheres also contain a small amount of carboxyl groups). $6 \times 10^3$ WNV-infected mice were injected with $4.41 \times 10^9$ 0.5 μm naked or carboxylated polystyrene beads or PLGA spheres when significant weight loss was detected. As can be seen in FIG. 12B, to date, PLGA naked and carboxylated spheres showed similar improvements in survival as carboxylated polystyrene beads.

To see if carboxylated PLGA spheres injected on d6 p.i. reduced infiltration of the d7 brain in $6 \times 10^4$ WNV-infected mice, we compared PBS, 0.5 μm carboxylated beads, 0.5 μm carboxylated PLGA spheres, and 0.5 μm carboxylated diamond particle treatment of mice with $4.41 \times 10^9$ particles delivered i.v. Brains, blood, spleen and liver were processed for flow cytometry. Analysis of this experiment is ongoing, however preliminary analysis of the brains of these mice show that all three particles successfully reduce infiltration of the brain by immune cells (FIG. 12C). Increases in total leukocytes in the spleen were also observed, consistent with the results we have seen in carboxylated bead treated mice.

Example 5

Bead Treatment in T-Cell Deficient Mice

Figure 13:
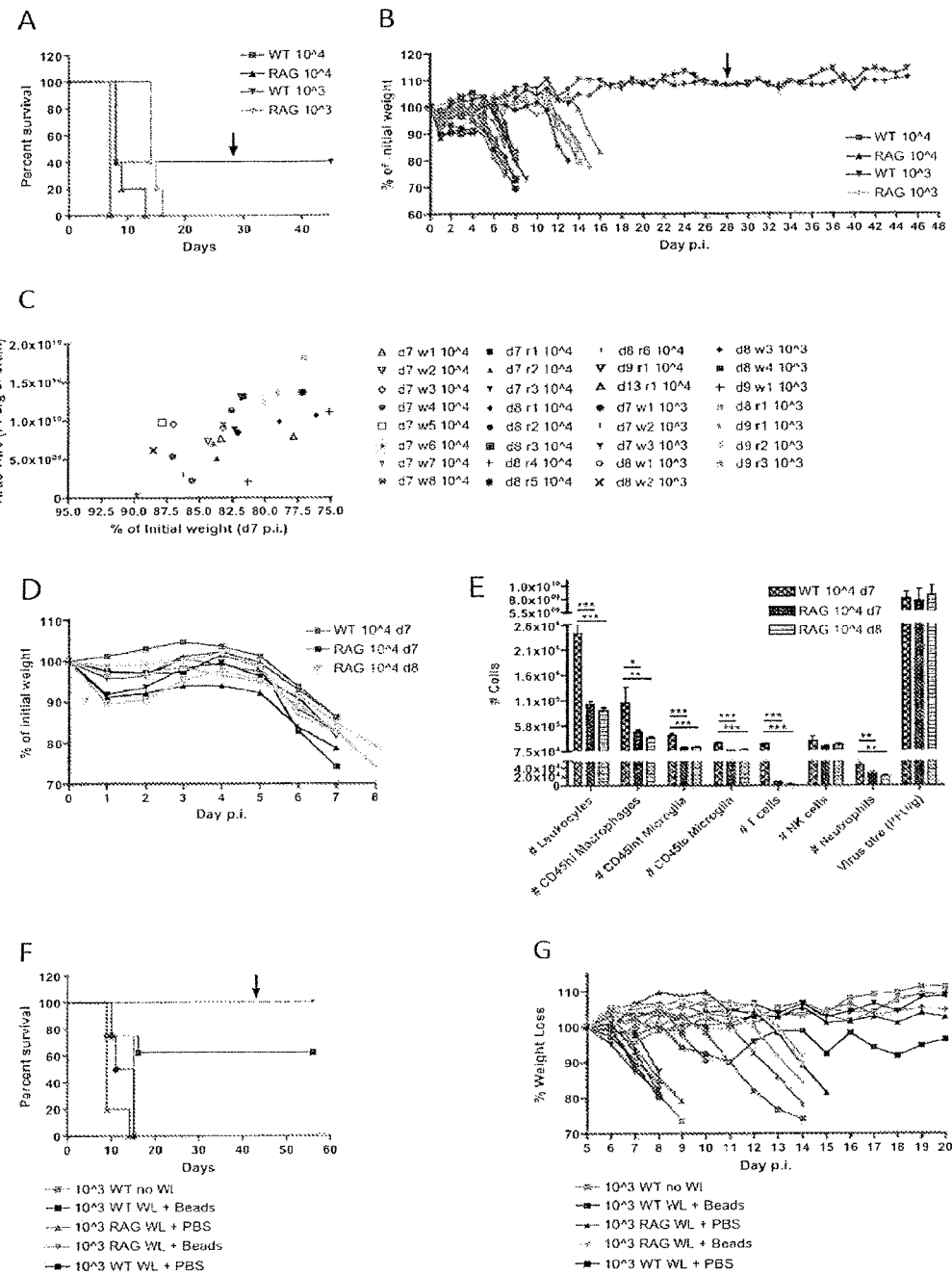
FIG. 13 shows (A) the percent survival and (B) weight loss in wild-type and T cell deficient mice infected with high or low dose WNV; (C) the correlation between weight loss and viral titers in the brains of wild-type and T cell deficient mice infected with high or low dose WNV; (D) weight loss (E) and immune cell infiltration into the brains of wild type and T cell deficient mice infected with high dose WNV at day 8 post infection; (F) percent survival (G) and weight loss of wild-type and T cell deficient mice infected with high or low dose WNV and treated with carboxylated beads or PBS upon significant weight loss.

C57BL/6 wildtype (WT) and RAG (T cell-deficient) mice were infected with $6 \times 10^4$ or $6 \times 10^3$ PFU WNV. WT mice infected with the high dose of $6 \times 10^4$ showed 100% mortality on d7 p.i., while RAG mice infected with the same dose began to die on d8 p.i., with some mice living up to d13 p.i. WT mice infected with the lower dose of $6 \times 10^3$ showed 60% mortality by d8 p.i., but 40% long-term survival after this time point. RAG mice infected with this same dose did not begin to die until d14 p.i., however by d16 all RAG mice were dead (FIG. 13A-B). These data suggest either a direct or indirect role for T cells in the immunopathology of WNV encephalitis, as T cell deficient mice survive for longer than RAGS. However, it also highlights the point that T cells are critical to control viral infection, as all of the RAG mice infected with the low dose succumb to disease whereas 40% of the WT mice survive with immunity.

The weight loss of these mice was recorded daily, and it was shown that weight loss precedes death in both RAGS and WT mice (FIG. 13B). However, it was observed that WT only live for a maximum of 2-3 days after initial weight loss, while RAGS could live up to 5 days after weight loss had begun. Plaque assay of brains harvested from RAG and WT mice infected with either $6 \times 10^4$ or $6 \times 10^3$ revealed that percentage weight loss strongly correlated with virus titre (FIG. 12C). In general, RAG mice showed greater weight loss at time of death and higher titres of virus than WT mice. It appears that this may be attributed to the fact that they were able to survive for longer than WT mice after initial weight loss, and thus virus continued to increase in the brain and the mice continued to lose weight until time of death, as opposed to directly being a result of not being able to control virus without T cells. This hypothesis is supported by the flow cytometry of the brain (FIG. 13D-E) in which d7 WT and d7/d8 RAG mice brains were compared. RAG mice show a significant reduction in infiltration of the brain by macrophages, microglia, T cells (as they are deficient) and neutrophils, which does not increase between d7 and d8 p.i. This may explain why these animals survive longer than WT mice after initial weight loss if immunopathology is the main contributor to death of these animals.

RAG and WT mice were also infected with $6 \times 10^3$ PFU WNV and were weighed daily in order to test the efficacy of carboxylated beads in the absence of T cells. Upon significant weight loss (>4% in 24 hours) mice were treated with $4.41 \times 10^9$ carboxylated beads or PBS i.v. delivered in a 300 ul volume. There was no significant improvement in survival of RAG mice by bead injection (FIG. 12F). RAG mice continued to lose weight after bead or PBS injection and died 2-5 days later (FIG. 12G). This experiment needs to be repeated again to confirm results.

Example 6

Bead Treatment in EAE

C57BL/6 mice will be primed with MOG and CFA adjuvant. At the time of disease symptom development, as determined by changes in gait, posture and other activities, carboxylated particles will be administered intravenously, either very 8 hours, every 16 hours, every day or every 48 hours. The severity of disease will be determined by changes in disease score. Infusion of particles will prevent migration of monocytes into the brain and subsequent T cell priming resulting in significant reductions in disease scores.

Example 7

Bead Treatment in Atherosclerosis and Neointimal Smooth Muscle Cell Proliferation APO/E deficient mice will be fed a high fat diet. From 4 weeks of age, carboxylated particles will be administered intravenously, every 8 hours, every 16 hours, every 24 hours, every 48 hours, every 72 hours, once weekly, or once monthly. The severity of disease will be determined by changes in arterial histology. Infusion of particles will prevent migration of monocytes into the arterial wall and prevent subsequent immune sequelae critical to drive smooth muscle proliferation and intimal plaque formation.

While specific embodiments of the invention have been described and illustrated, such embodiments should be considered illustrative of the invention only and not as limiting the invention as construed in accordance with the accompanying claims.

All patents, applications and other references cited herein are incorporated by reference in their entireties.

What is claimed is:

1. A method of ameliorating an inflammatory immune response in a subject in need thereof comprising intravenously administering to the subject a pharmaceutical composition comprising poly(lactic-co-glycolic acid) (PLGA) particles that have been modified to contain one or more carboxyl groups on the particle's surface, wherein the particles do not comprise one or more therapeutically active ingredients.

2. The method of claim 1, wherein the particles are spherical particles.

3. The method of claim 2, wherein the particles have a diameter of between about 0.1 µm to about 10 µm.

4. The method of claim 2, wherein the particles have a diameter of between about 0.3 µm to about 5 µm.

5. The method of claim 2, wherein the particles have a diameter of between about 0.5 µm to about 1 µm.

6. The method of claim 2, wherein the particles have a diameter of about 0.5 µm.

7. The method of claim 1, wherein the subject has a viral infection.

8. The method of claim 7, wherein the viral infection is a West Nile Virus infection.

9. The method of claim 1, wherein the PLGA particles have been modified from naked PLGA particles.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Mus sp.

<400> SEQUENCE: 1

```
Met Glu Val Gly Trp Tyr Arg Ser Pro Phe Ser Arg Val Val His Leu
1               5                   10                  15

Tyr Arg Asn Gly Lys
            20
```